US010577347B2

(12) United States Patent
Axt et al.

(10) Patent No.: US 10,577,347 B2
(45) Date of Patent: *Mar. 3, 2020

(54) CRYSTALLINE FORMS OF A BIPHENYL COMPOUND

(71) Applicant: THERAVANCE BIOPHARMA R&D IP, LLC, South San Francisco, CA (US)

(72) Inventors: Sabine Axt, Sunnyvale, CA (US); Timothy J. Church, San Mateo, CA (US)

(73) Assignee: Theravance Biopharma R&D IP, LLC, South San Francisco, CA (US)

(*) Notice: Subject to any disclaimer, the term of this patent is extended or adjusted under 35 U.S.C. 154(b) by 129 days.

This patent is subject to a terminal disclaimer.

(21) Appl. No.: 15/486,796

(22) Filed: Apr. 13, 2017

(65) Prior Publication Data
US 2018/0051004 A1 Feb. 22, 2018

Related U.S. Application Data

(60) Continuation of application No. 14/974,980, filed on Dec. 18, 2015, now Pat. No. 9,656,993, which is a continuation of application No. 14/552,893, filed on Nov. 25, 2014, now Pat. No. 9,249,099, which is a division of application No. 14/219,296, filed on Mar. 19, 2014, now Pat. No. 8,921,395, which is a division of application No. 13/740,465, filed on Jan. 14, 2013, now Pat. No. 8,716,313, which is a division of application No. 12/817,543, filed on Jun. 17, 2010, now Pat. No. 8,377,965, which is a continuation of application No. 12/563,788, filed on Sep. 21, 2009, now abandoned, which is a continuation of application No. 11/890,880, filed on Aug. 8, 2007, now Pat. No. 7,700,777, which is a continuation of application No. 11/371,445, filed on Mar. 9, 2006, now abandoned.

(60) Provisional application No. 60/660,208, filed on Mar. 10, 2005.

(51) Int. Cl.
| C07D 401/12 | (2006.01) |
| A61K 9/00 | (2006.01) |
| A61K 9/14 | (2006.01) |
| A61K 9/19 | (2006.01) |
| A61K 31/4545 | (2006.01) |
| A61K 31/58 | (2006.01) |
| C07D 211/62 | (2006.01) |
| A61K 31/13 | (2006.01) |
| A61K 33/42 | (2006.01) |
| A61K 31/56 | (2006.01) |
| A61K 45/00 | (2006.01) |
| A61K 45/06 | (2006.01) |
| A61M 15/00 | (2006.01) |
| C07D 211/94 | (2006.01) |

(52) U.S. Cl.
CPC .......... *C07D 401/12* (2013.01); *A61K 9/0073* (2013.01); *A61K 9/14* (2013.01); *A61K 9/19* (2013.01); *A61K 31/13* (2013.01); *A61K 31/4545* (2013.01); *A61K 31/56* (2013.01); *A61K 31/58* (2013.01); *A61K 33/42* (2013.01); *A61K 45/00* (2013.01); *A61K 45/06* (2013.01); *A61M 15/00* (2013.01); *C07D 211/62* (2013.01); *C07D 211/94* (2013.01); *A61M 2202/064* (2013.01); *C07B 2200/13* (2013.01)

(58) Field of Classification Search
CPC .. C07D 401/12; C07D 211/94; C07D 211/62; A61M 15/00; A61M 2202/064; A61K 45/06; A61K 31/56; A61K 45/00; A61K 31/58; A61K 9/19; A61K 9/0073; A61K 9/14; A61K 31/4545; A61K 33/42; A61K 31/13; C07B 2200/13
See application file for complete search history.

(56) References Cited

U.S. PATENT DOCUMENTS

| 3,903,137 | A | 9/1975 | Miura et al. |
| 6,240,918 | B1 | 6/2001 | Ambrosio et al. |
| 6,693,202 | B1 | 2/2004 | Aggen et al. |
| 7,288,657 | B2 | 10/2007 | Mammen et al. |
| 7,399,863 | B2 | 7/2008 | Linsell et al. |
| 7,524,880 | B2 | 4/2009 | Li et al. |
| 7,585,879 | B2 | 9/2009 | Mammen et al. |
| 7,700,777 | B2 | 4/2010 | Axt et al. |

(Continued)

FOREIGN PATENT DOCUMENTS

EP 0747355 A1 12/1996

OTHER PUBLICATIONS

Ahuja, "Handbook of Modern Pharmaceutical Analysis", Voulme 3, pp. 187-188 (2001).

(Continued)

*Primary Examiner* — John Pak
*Assistant Examiner* — Andriae M Holt
(74) *Attorney, Agent, or Firm* — Jeffrey A. Hagenah

(57) ABSTRACT

The invention provides crystalline forms of biphenyl-2-ylcarbamic acid 1-(2-{[4-(4-carbamoylpiperidin-1-ylmethyl)benzoyl]methylamino}ethyl)piperidin-4-yl ester, and pharmaceutically acceptable solvates thereof. The crystalline form can be a freebase, or a salt such as a diphosphate, monosulfate or dioxalate salt. The invention also provides pharmaceutical compositions comprising these crystalline compounds or prepared using these compounds; processes and intermediates for preparing the crystalline compounds; and methods of using these compounds to treat a pulmonary disorder.

7 Claims, 13 Drawing Sheets

(56) References Cited

U.S. PATENT DOCUMENTS

| | | |
|---|---|---|
| 7,910,608 B2 | 3/2011 | Mammen et al. |
| 8,034,946 B2 | 10/2011 | Mammen et al. |
| 8,037,880 B2 | 10/2011 | Zhu et al. |
| 8,053,448 B2 | 11/2011 | Mammen et al. |
| 8,242,137 B2 | 8/2012 | Axt et al. |
| 8,377,965 B2 | 2/2013 | Axt et al. |
| 9,656,993 B2 | 5/2017 | Axt et al. |
| 2003/0018019 A1 | 1/2003 | Meade et al. |
| 2005/0113413 A1 | 5/2005 | Wilson et al. |
| 2005/0203133 A1* | 9/2005 | Mammen ............ C07D 211/62 514/316 |
| 2006/0205949 A1 | 9/2006 | Dalziel et al. |
| 2007/0112027 A1 | 5/2007 | Axt et al. |
| 2010/0048622 A1 | 2/2010 | Axt et al. |

OTHER PUBLICATIONS

Axt et al., "Crystalline forms of biphenyl-2-ylcarbamic acid 1-[2-[[4-(4-carbamoylpiperidin-1-ylmethyl)benzoyl]methylamino]ethyl]piperidin-4-yl ester and their salts", CAPLUS: 145:356657 (2006).
Bernstein, "Polymorphism in Molecular Crystals", Clarendon Press, Oxford, pp. 117 (2002).
Bernstein, "Polymorphism in Molecular Crystals", Clarendon Press, Oxford, pp. 271-272 (2002).
Braga et al., "Making crystals from crystals: a green route to crystal engineering and polymorphism", Chem. Comm., pp. 3635-3645 (2005).
Brittain, "Polymorphism in Pharmaceutical Solids", Marcel Dekker, Inc., New York, New York, p. 202 (1999).
Byrn et al., "Solid-State Chemistry of Drugs", Second Ed., SSCI, Inc., West Lafayette, Indiana, p. 63 (1999).
Calleri et al., "Synthetic epsomite, MgSO4. 7H2O: absolute configuration and surface features of the complementary {111} forms", CAPLUS: 101:15411 (1984).
Clarke et al., "Structure-stability relationships in cocrystal hydrates: does the promiscuity of water make crystalline hydrates the nemesis of crystal engineering?", Crystal Growth & Design, vol. 10, No. 5, pp. 2152-2167 (2010).
Dean, "Analytical Chemistry Handbook", McGraw-Hill, Inc., New York, New York, pp. 10.24-10.26 (1995).
Doelker, "Physicochemical behavior of active substances. Consequences for the feasibility and stability of pharmaceutical forms", CAPLUS: 132:325872 (2000) and Doelker, S.T.P. Pharma Pratiques (1999), 9(5) 399-409 (in French).
Doelker, "Crystalline modifications and polymorphism changes during drug manufacturing", CAPLUS: 138:3209993 (2002) and Doelker, Annales Pharmaceutiques Francaises (2002), 60(3), 161-176 (in French).
Griffith, "Thermogravimetric analysis of complex mixtures of hydrates", Analytical Chemistry, vol. 29(2) pp. 198-202 (1957).
Hilfiker, "Polymorphism: In the Pharmaceutical Industry", Wiley-VCH, Weinheim, Germany, p. 359 (2006).
Jain et al., "Polymorphism in Pharmacy", Indian Drugs, 23 (6), pp. 315-329 (1986).
Muzaffar et al., "Polymorphism and Drug Availability", Journal of Pharmacy (Lahore), 1(1) pp. 59-66 (1979).
Otsuka et al., "Effect of polymorphism forms of bulk powders on pharmaceutical properties of carbamazepine granules", Chem. Pharm. Bull., 47(6) pp. 852-856 (1999).
Seddon, "Pseudopolymorph: A Polemic", Crystal Growth & Design, 4(6) p. 1087 (2004)(2 pages from Internet).
Taday et al., "Using terahertz pulse spectroscopy to study the crystalline structure of a drug: A case study of the polymorphs of ranitidine hydrochloride", Journal of Pharmaceutical Sciences, vol. 92, No. 4, pp. 831-838 (2003).
Ulrich, "Crystallization", Kirk-Othmer Encyclopedia of Chemical Technology, John Wiley & Sons, Hoboken, New Jersey, vol. 8, pp. 95-147 (2002).
USPTO Advisory Action dated Aug. 14, 2009 for U.S. Appl. No. 11/371,445.
USPTO Final Rejection dated Jul. 27, 2009 for U.S. Appl. No. 11/371,445.
USPTO Non-Final Rejection dated Nov. 4, 2008 for U.S. Appl. No. 11/890,880.
USPTO Non-Final Rejection dated Feb. 12, 2009 for U.S. Appl. No. 11/890,880.
USPTO Non-Final Rejection dated Mar. 16, 2009 for U.S. Appl. No. 11/371,445.
Wikipedia, "Micronization" (2011).
Wikipedia, "Water of Crystallization" (2011).

* cited by examiner

CRYSTALLINE FORMS OF A BIPHENYL COMPOUND

CROSS-REFERENCE TO RELATED APPLICATIONS

This application is a continuation of U.S. application Ser. No. 14/974,980, filed on Dec. 18, 2015; which application is a continuation of U.S. application Ser. No. 14/552,893, filed on Nov. 25, 2014 (now U.S. Pat. No. 9,249,099 B2); which application is a divisional of U.S. application Ser. No. 14/219,296, filed on Mar. 19, 2014 (now U.S. Pat. No. 8,921,395 B2); which application is a divisional of U.S. application Ser. No. 13/740,465, filed on Jan. 14, 2013 (now U.S. Pat. No. 8,716,313 B2); which application is a divisional of U.S. application Ser. No. 12/817,543, filed on Jun. 17, 2010 (now U.S. Pat. No. 8,377,965 B2); which application is a continuation of U.S. Ser. No. 12/563,788, filed on Sep. 21, 2009 (now abandoned); which application is a continuation of U.S. Ser. No. 11/890,880, filed on Aug. 8, 2007 (now U.S. Pat. No. 7,700,777 B2); which application is a continuation of U.S. Ser. No. 11/371,445, filed Mar. 9, 2006 (now abandoned); which claims the benefit of U.S. Provisional Application No. 60/660,208, filed on Mar. 10, 2005; the entire disclosures of which are incorporated herein by reference in their entirety.

BACKGROUND OF THE INVENTION

Field of the Invention

The present invention relates to novel crystalline forms of a biphenyl compound and solvates thereof, which are expected to be useful for treating pulmonary disorders. The invention also relates to pharmaceutical compositions comprising the crystalline compounds or prepared from such compounds, processes and intermediates for preparing such crystalline compounds and methods of using such compounds to treat a pulmonary disorder.

State of the Art

Commonly-assigned U.S. Patent Publication No. 2005/0203133 to Mammen et al. discloses novel biphenyl compounds that are expected to be useful for treating pulmonary disorders such as chronic obstructive pulmonary disease (COPD) and asthma. In particular, the compound biphenyl-2-ylcarbamic acid 1-(2-{[4-(4-carbamoylpiperidin-1-ylmethyl)benzoyl]methylamino}ethyl)piperidin-4-yl ester is specifically described in this application as possessing muscarinic receptor antagonist or anticholinergic activity.

The chemical structure of biphenyl-2-ylcarbamic acid 1-(2-{[4-(4-carbamoyl piperidin-1-ylmethyl)benzoyl]methylamino}ethyl)piperidin-4-yl ester is represented by formula I:

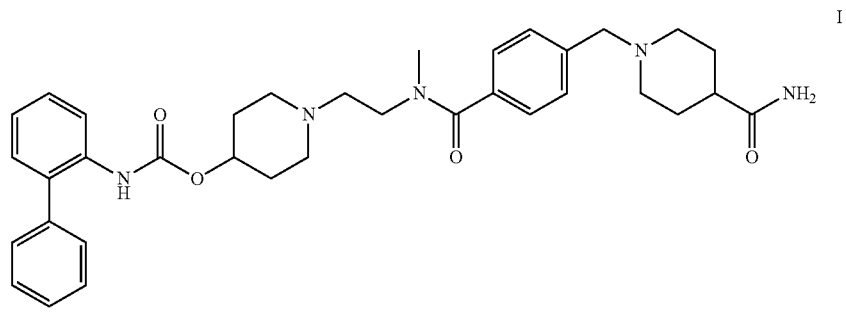 [SMILES: CN(CCN1CCC(OC(=O)Nc2ccccc2-c2ccccc2)CC1)C(=O)c1ccc(CN2CCC(C(N)=O)CC2)cc1]

The compound of formula I has been named using the commercially-available AutoNom software (MDL, San Leandro, Calif.).

Therapeutic agents useful for treating pulmonary or respiratory disorders are advantageously administered directly into the respiratory tract by inhalation. In this regard, several types of pharmaceutical inhalation devices have been developed for administering therapeutic agents by inhalation including dry powder inhalers (DPI), metered-dose inhalers (MDI) and nebulizer inhalers. When preparing pharmaceutical compositions and formulations for use in such devices, it is highly desirable to have a crystalline form of the therapeutic agent that is neither hygroscopic nor deliquescent and which has a relatively high melting point (typically greater than about 150° C.) thereby allowing the material to be micronized without significant decomposition.

No crystalline forms of the compound of formula I have been reported previously. Accordingly, a need exists for a stable, non-deliquescent crystalline forms of the compound of formula I which have acceptable levels of hygroscopicity and relatively high melting points.

SUMMARY OF THE INVENTION

The present invention provides crystalline forms of biphenyl-2-ylcarbamic acid 1-(2-{[4-(4-carbamoylpiperidin-1-ylmethyl)benzoyl]methylamino}ethyl)piperidin-4-yl ester (formula I). The crystalline form can be a freebase, a pharmaceutically acceptable salt such as a diphosphate, monosulfate or dioxalate salt, or a pharmaceutically acceptable solvate of such salt.

Surprisingly, crystalline forms of the invention have been found not to be deliquescent, even when exposed to atmospheric moisture. Additionally, the crystalline forms of the invention have acceptable levels of hygroscopicity and acceptable melting points, greater than about 70° C. For example, the diphosphate salt has a melting point around 150° C.

Among other uses, crystalline forms of the compound of formula I are useful for preparing pharmaceutical compositions expected to have utility in treating pulmonary disorders. Accordingly, one aspect of the invention pertains to a pharmaceutical composition comprising a pharmaceutically acceptable carrier and a therapeutically effective amount of a crystalline form of the compound of formula I.

Yet another aspect of the invention pertains to compositions comprising a crystalline form of the compound of formula I in combination with one or more other therapeutic agents. Accordingly, in one embodiment, the invention is directed to a composition comprising (a) a pharmaceutically acceptable carrier and a therapeutically effective amount of a crystalline form of the compound of formula I; and (b) a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the crystalline form and the agent are formulated together or separately. When the agent is formulated separately, a pharmaceutically acceptable carrier may be included.

Another aspect of the invention relates to a pharmaceutical composition comprising an aqueous isotonic saline solution comprising a crystalline form of the compound of formula I, wherein the solution has a pH in the range of from about 4 to 6. In a particular embodiment, an aqueous nebulizer formulation is buffered with citrate buffer to a pH of about 5. In another particular embodiment, the aqueous nebulizer formulation contains about 0.5 mg/mL free base equivalents of biphenyl-2-ylcarbamic acid 1-(2-{[4-(4-carbamoylpiperidin-1-ylmethyl)benzoyl]methylamino}ethyl) piperidin-4-yl ester.

In one embodiment, this invention provides a drug delivery device comprising a dry powder inhaler containing a pharmaceutical composition comprising a pharmaceutically acceptable carrier and a crystalline form of the compound of formula I.

The compound of formula I has muscarinic receptor antagonist activity. Accordingly, crystalline forms of the compound of formula I are useful for treating pulmonary disorders such as asthma and chronic obstructive pulmonary disease. Thus, another aspect of the invention pertains to a method for treating a pulmonary disorder comprising administering to a patient a therapeutically effective amount of a crystalline form of the compound of formula I. Still another aspect of the invention relates to a method of producing bronchodilation in a patient comprising administering to the patient a bronchodilation-producing amount of a crystalline form of the compound of formula I. In one embodiment, the compound is administered by inhalation. The invention also provides a method of treating chronic obstructive pulmonary disease or asthma comprising administering to a patient a therapeutically effective amount of a crystalline form of the compound of formula I. Another aspect of the invention is directed to a method for antagonizing a muscarinic receptor in a mammal comprising administering to the mammal a therapeutically effective amount of a crystalline form of the compound of formula I.

The invention is also directed to processes for preparing crystalline forms of the compound of formula I. The invention also provides a process for purifying the compound of formula I comprising forming a crystalline salt or a crystalline freebase of biphenyl-2-ylcarbamic acid 1-(2-{[4-(4-carbamoylpiperidin-1-ylmethyl)benzoyl]methylamino}ethyl) piperidin-4-yl ester. The invention is further directed to products prepared by the processes described herein.

The invention is also directed to a crystalline form of the compound of formula I in a micronized form; and to pharmaceutical compositions comprising a pharmaceutically acceptable carrier and a micronized crystalline form of the compound of formula I.

The invention is also directed to a crystalline form of the compound of formula I for use in therapy or as a medicament. Additionally, the invention relates to the use of a crystalline form of the compound of formula I for the manufacture of a medicament; especially for the manufacture of a medicament for the treatment of a pulmonary disorder or for antagonizing a muscarinic receptor in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
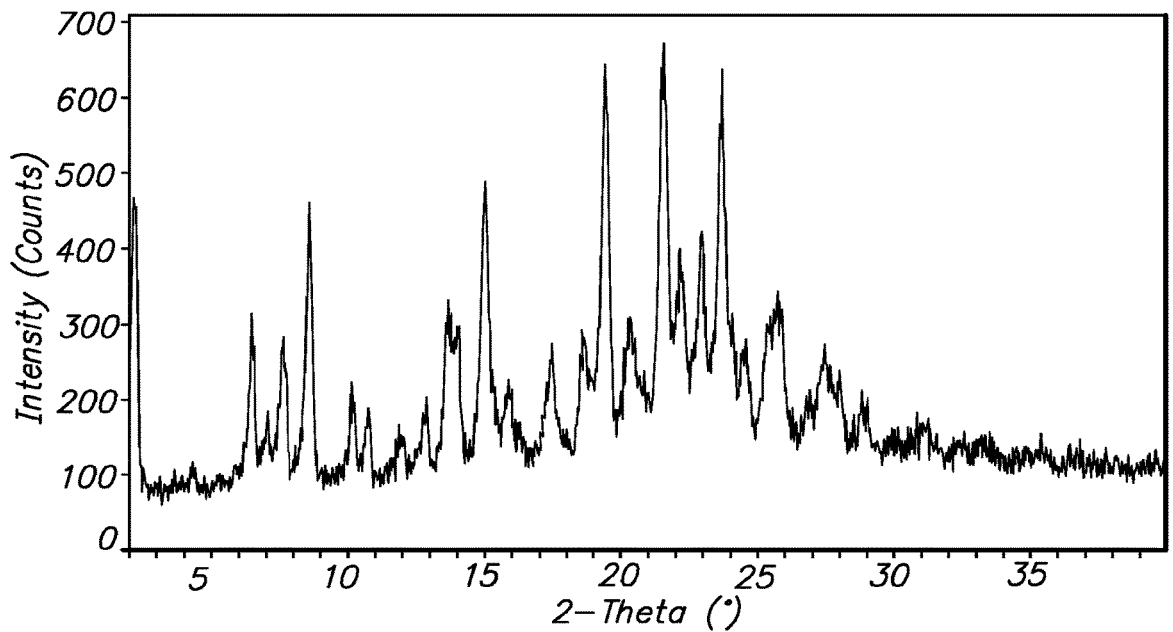
FIG. 1 shows a powder x-ray diffraction (PXRD) pattern of a crystalline diphosphate salt of biphenyl-2-ylcarbamic acid 1-(2-{[4-(4-carbamoylpiperidin-1-ylmethyl)benzoyl]methylamino}ethyl)piperidin-4-yl ester (the compound of formula I).

The invention provides crystalline forms of biphenyl-2-ylcarbamic acid 1-(2-{[4-(4-carbamoylpiperidin-1-ylmethyl)benzoyl]methylamino}ethyl)piperidin-4-yl ester. The crystalline form can be a freebase, a pharmaceutically acceptable salt such as a diphosphate, monosulfate or dioxalate salt, or a pharmaceutically acceptable solvate of such salt. In a particular embodiment, the crystalline form is a diphosphate salt.

Definitions

When describing the compounds, compositions, methods and processes of the invention, the following terms have the following meanings unless otherwise indicated.

The term "solvate" means a complex or aggregate formed by one or more molecules of a solute, i.e. a crystalline compound of formula I, and one or more molecules of a solvent. Such solvates typically have a substantially fixed molar ratio of solute and solvent. This term also includes clathrates, including clathrates with water. Representative solvents include, by way of example, water, methanol, ethanol, isopropanol, acetic acid and the like. When the solvent is water, the solvate formed is a hydrate.

The term "Form I" refers to the crystalline freebase that is prepared by a method that uses water as part of a solvent mixture as the inert diluent. The term "Form II" refers to the crystalline freebase that is prepared by a method that uses an organic solvent mixture as the inert diluent, i.e. no water.

The term "therapeutically effective amount" means an amount sufficient to effect treatment when administered to a patient in need of treatment. For example, a therapeutically effective amount for antagonizing a muscarinic receptor is that amount which will achieve the desired antagonizing effect. Similarly, a therapeutically effective amount for treating a pulmonary disorder is that amount that will achieve the desired therapeutic result, which may be disease prevention, amelioration, suppression or alleviation, as described below.

The term "treating" or "treatment" as used herein means the treating or treatment of a disease or medical condition (such as COPD) in a patient such as a mammal (particularly a human) that includes:

(a) preventing the disease or medical condition from occurring, i.e., prophylactic treatment of a patient believed to be at risk of contracting or being predisposed to such disease or medical condition;

(b) ameliorating the disease or medical condition, i.e., eliminating or causing regression of the disease or medical condition in a patient having such disease or medical condition;

(c) suppressing the disease or medical condition, i.e., slowing or arresting the development of the disease or medical condition in a patient having such disease or medical condition; or (d) alleviating the symptoms of the disease or medical condition in a patient having such disease or medical condition.

The term "pharmaceutically acceptable" refers to a material that is not biologically or otherwise undesirable. For example, the term "pharmaceutically acceptable carrier" refers to a material that can be incorporated into a composition and administered to a patient without causing undesirable biological effects or interacting in a deleterious manner with other components of the composition. Such pharmaceutically acceptable materials typically have met the required standards of toxicological and manufacturing testing, and include those materials identified as suitable inactive ingredients by the U.S. Food and Drug administration.

The term "unit dosage form" refers to a physically discrete unit suitable for dosing a patient, i.e., each unit containing a predetermined quantity of a compound of the invention calculated to produce the desired therapeutic effect either alone or in combination with one or more additional units. For example, such unit dosage forms may be capsules, tablets, pills, and the like.

Synthesis

The crystalline compounds of the invention can be synthesized from readily available starting materials as described below and in the Examples. It will be appreciated that while specific process conditions (i.e. reaction temperatures, times, mole ratios of reactants, solvents, pressures, etc.) are given, other process conditions can also be used unless otherwise stated. Generally, the reactions are conducted in a suitable inert diluent, examples of which include, but are not limited to, methanol, ethanol, isopropanol, isobutanol, ethyl acetate, acetonitrile, dichloromethane, methyl t-butyl ether, and the like, and mixtures thereof, typically containing water. Upon completion of any of the foregoing reactions, the crystalline compounds can be isolated from the reaction mixture by any conventional means such as precipitation, concentration, centrifugation and the like.

The biphenyl-2-ylcarbamic acid 1-(2-{[4-(4-carbamoylpiperidin-1-ylmethyl)benzoyl]methylamino}ethyl)piperidin-4-yl ester employed in the invention can be readily prepared from commercially available starting materials and reagents using the procedures described in the Examples, or using the procedures described in U.S. Patent Publication No. 2005/0203133 to Mammen et al.

The molar ratios described in the methods of the invention can be readily determined by various methods available to those skilled in the art. For example, such molar ratios can be readily determined by $^1$H NMR. Alternatively, elemental analysis and HPLC methods can be used to determine the molar ratio.

Diphosphate Salt Crystal

A diphosphate salt of the invention typically contains between about 1.8 and 2.2 molar equivalents of phosphate per molar equivalent of the compound of formula I; including between about 1.9 and 2.1 molar equivalents of phosphate per molar equivalent of the compound of formula I.

In general, a crystalline diphosphate salt of the compound of formula I or a pharmaceutically acceptable solvate thereof can be prepared by contacting biphenyl-2-ylcarbamic acid 1-(2-{[4-(4-carbamoylpiperidin-1-ylmethyl)benzoyl] methylamino}ethyl)piperidin-4-yl ester with phosphoric acid. For example, the ester can be contacted with dilute aqueous phosphoric acid to form an amorphous diphosphate salt, which is then contacted with an inert diluent.

To prepare the amorphous diphosphate salt, the ester is typically dissolved in aqueous phosphoric acid, diluted with water and isolated by lyophilization. Generally, this reaction is conducted at a temperature ranging from about 0 to 30° C., such as about 24° C. The ratio of milligrams of the ester to microliters of 1M phosphoric acid is about 1:3 to about 1:4, including about 1:3.5. The resulting amorphous diphosphate salt is then typically contacted with about 15 mg/ml to about 25 mg/ml of inert diluent. Generally, this reaction is conducted at a temperature ranging from about 50 to 70° C., such as about 60° C.

In a particular embodiment, 500 mg of the ester is taken up in 5 ml of water and 1.5 ml of 1M phosphoric acid. The pH is adjusted to approximately pH 5.3 with additional 1M phosphoric acid (equaling 2.1 molar equivalents). The clear solution is filtered, frozen and lyophilized to dryness to provide an amorphous diphosphate salt. The resulting amorphous diphosphate salt is added to an isopropanol:acetonitrile (1:1) solution, followed by the addition of water. In this reaction, the ratio of milligrams of the amorphous diphosphate salt to milliliters of isopropanol:acetonitrile is about 2:0.9 to about 2:2, including about 2:1.

Alternatively, a crystalline diphosphate salt can be prepared by contacting the ester with about 2.0 to about 2.1 molar equivalents of phosphoric acid. Generally, this reaction is conducted in an inert diluent at a temperature ranging from about 40 to 60° C., such as about 50° C. In a particular embodiment, the ester is added to an isopropanol:acetonitrile (1:1) solution, followed by the addition of water. After heating, phosphoric acid is added. In this reaction, the ratio of grams of the ester to milliliters of phosphoric acid is about 5:14 to about 5:18, including about 5:16.

Figure 6:
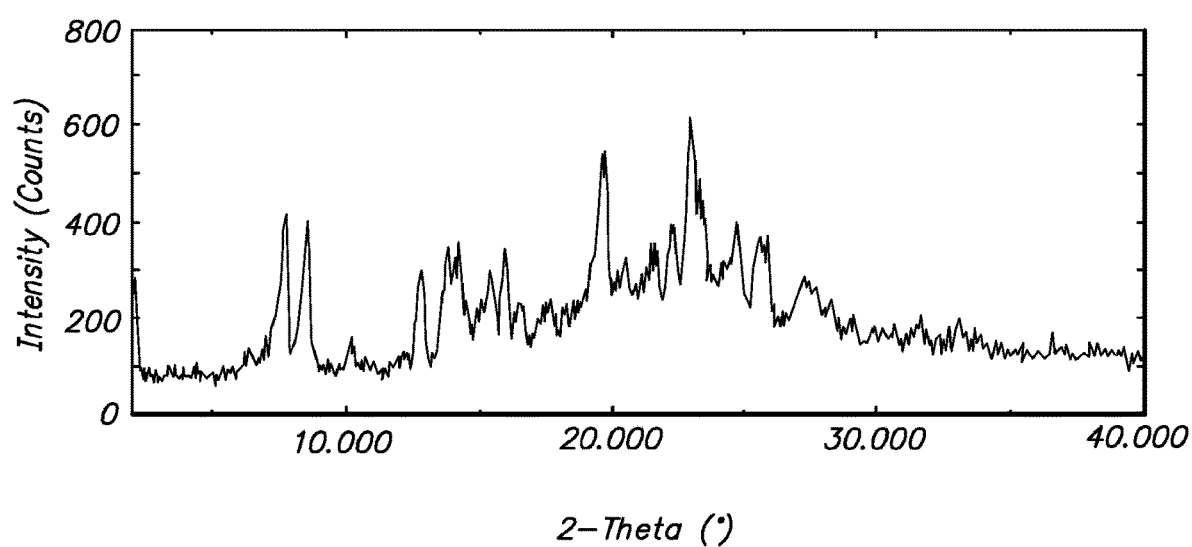
FIG. 6 and FIG. 7 show a PXRD pattern and a DSC trace, respectively, for a less stable form of a crystalline diphosphate salt.
Figure 7:
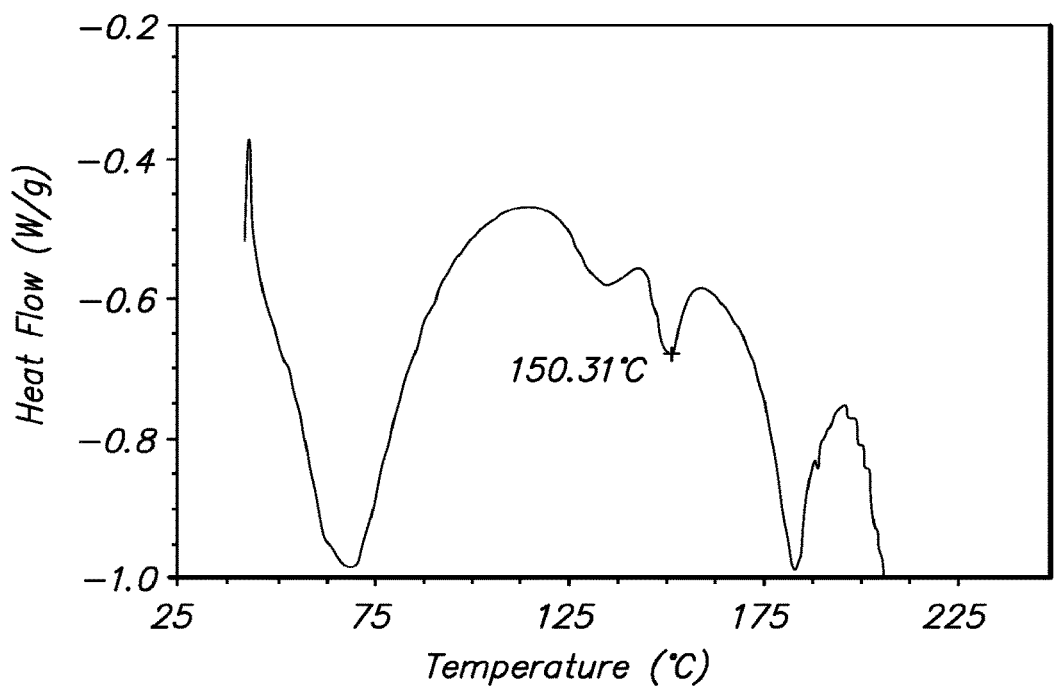

Both of the aforementioned processes for preparing crystalline diphosphate salts can lead to the formation of a separate, less stable, diphosphate crystal form. FIG. 6 and FIG. 7 show a PXRD pattern and a DSC trace, respectively, for this less stable form. The more stable diphosphate crystal is the prevalent form; however, when the less stable diphosphate form is present, it can be readily converted to the more stable crystal by increasing the water content in the solvent mixture, and reheating the suspension to about 50° C. to about 70° C., typically about 60° C., for about 2 to about 6 hours, typically about 2 hours, followed by cooling to room temperature overnight with slow stirring.

Monosulfate Salt Crystal

A monosulfate salt of the invention typically contains between about 0.8 and 1.2 molar equivalents of sulfate per molar equivalent of the compound of formula I; including between about 0.9 and 1.1 molar equivalents of sulfate per molar equivalent of the compound of formula I.

A crystalline monosulfate salt of the compound of formula I or a pharmaceutically acceptable solvate thereof can be prepared by contacting biphenyl-2-ylcarbamic acid 1-(2-{[4-(4-carbamoylpiperidin-1-ylmethyl)benzoyl]methylamino}ethyl) piperidin-4-yl ester with sulfuric acid. For example, the ester can be contacted with 1N aqueous sulfuric acid to form a monosulfate salt, which is then contacted with an inert diluent.

To prepare the monosulfate salt, the ester is typically dissolved in 1:1 acetonitrile:water, diluted with aqueous sulfuric acid, diluted with water and isolated by lyophilization. Generally, this reaction is conducted at a temperature ranging from about 0 to 30° C., such as about 24° C. The ratio of milligrams of the ester to milliliters of 1N sulfuric acid in water is about 325 mg/ml to about 285 mg/ml, including about 305 mg/ml. In one particular embodiment, 442 mg of the ester is taken up in 5 ml of 1:1 acetonitrile:water and 1.45 ml of 1N sulfuric acid is added slowly, while monitoring the pH. The pH is then adjusted to approximately pH 3.3. The clear solution is filtered, frozen and lyophilized to dryness to provide a monosulfate salt. The resulting monosulfate salt is then typically contacted with about 10 mg/ml to about 20 mg/ml of inert diluent. In one embodiment, this reaction is conducted at a first temperature and then at a lower second temperature, both temperatures ranging from about 50 to 80° C., such as about 60° C. to 70° C. In a particular embodiment, the monosulfate salt is added to an isopropanol:acetonitrile (10:1) solution. In this reaction, the ratio of milligrams of the monosulfate salt to milliliters of isopropanol:acetonitrile is about 15:3 to about 15:0.8, including about 15:1.

In another embodiment, this reaction is conducted at a first temperature and then at two lower temperature cycles. The first temperature ranges from about 50 to 80° C., such as about 70° C. The first lower temperature cycle varies from about 60° C. to 30° C. The second lower temperature cycle varies from about 40° C. to 30° C. In a particular embodiment, the monosulfate salt is added to an isopropanol:acetonitrile (10:1) solution. In this reaction, the ratio of milligrams of the monohydrate salt to milliliters of isopropanol:acetonitrile is about 161:7 to about 161:11, including about 161:9.

Dioxalate Salt Crystal

A dioxalate salt of the invention typically contains between about 1.8 and 2.2 molar equivalents of oxalate per molar equivalent of the compound of formula I; including between about 1.9 and 2.1 molar equivalents of oxalate per molar equivalent of the compound of formula I.

A crystalline dioxalate salt of biphenyl-2-ylcarbamic acid 1-(2-{[4-(4-carbamoylpiperidin-1-ylmethyl)benzoyl]methylamino}ethyl)piperidin-4-yl ester or a pharmaceutically acceptable solvate thereof, can be prepared by contacting biphenyl-2-ylcarbamic acid 1-(2-{[4-(4-carbamoylpiperidin-1-ylmethyl)benzoyl]methylamino}ethyl)piperidin-4-yl ester with oxalic acid. For example, the ester can be contacted with 1M aqueous oxalic acid to form a dioxalate salt, which is then contacted with an inert diluent.

To prepare the dioxalate salt, the ester is typically dissolved in 1:1 acetonitrile:water, diluted with aqueous oxalic acid, diluted with water and isolated by lyophilization. Generally, this reaction is conducted at a temperature ranging from about 0 to 30° C., such as about 24° C. The ratio of milligrams of the ester to milliliters of 1M aqueous oxalic acid is about 320 mg/ml to about 280 mg/ml, including about 300 mg/ml. In one particular embodiment, 510 mg of the ester is taken up in 5 ml of 1:1 acetonitrile:water and 1.7 ml of 1M aqueous oxalic acid is added slowly, while monitoring the pH. The pH is adjusted to approximately pH 3.0. The clear solution is filtered, frozen and lyophilized to dryness to provide a dioxalate salt.

In one embodiment, the resulting dioxalate salt is then typically contacted with about 5 mg/ml to about 15 mg/ml of inert diluent. Generally, this reaction is conducted at a temperature ranging from about 50 to 70° C., such as about 60° C. In a particular embodiment, the dioxalate salt is added to an isopropanol:water (94:6) solution. In this reaction, the ratio of milligrams of the dioxalate salt to milliliters of isopropanol:water is about 10:0.8 to about 10:3, including about 10:1.

A crystalline dioxalate salt can also be prepared by forming a seed crystal of a crystalline dioxalate salt of the ester (synthesized as described above), forming a dioxalate salt of the ester by contacting the ester with oxalic acid and dissolving the salt in an inert diluent to form a solution, and adding the seed crystal to the solution.

In one embodiment, a dioxalate salt is typically contacted with about 5 mg/ml to about 15 mg/ml of inert diluent. Generally, this reaction is conducted at a first temperature ranging from about 50 to 70° C., such as about 60° C. The mixture is then cooled to a second temperature ranging from about 3 to 10° C., such as about 4° C. The seed crystal of a crystalline dioxalate salt of the ester is then added. In a particular embodiment, the dioxalate salt is added to an isopropanol:water (94:6) solution. In this reaction, the ratio of milligrams of the dioxalate salt to milliliters of isopropanol:water is about 150:10 to about 150:16, including about 150:13.

Freebase Crystal

A crystalline freebase biphenyl-2-ylcarbamic acid 1-(2-{[4-(4-carbamoylpiperidin-1-ylmethyl)benzoyl]methylamino}ethyl)piperidin-4-yl ester or a pharmaceutically acceptable solvate thereof, can be prepared by contacting biphenyl-2-ylcarbamic acid 1-(2-{[4-(4-carbamoylpiperidin-1-ylmethyl)benzoyl]methylamino}ethyl)piperidin-4-yl ester with an inert diluent.

To prepare one form of a crystalline freebase (Form I), the ester is typically contacted with about 5 mg/ml to about 15 mg/ml of inert diluent. Generally, this reaction is conducted at a temperature ranging from about 20 to 30° C., such as about 25° C. In a particular embodiment, the ester is added to a water:acetonitrile (1:1) solution. In this reaction, the ratio of milligrams of the ester to milliliters of water: acetonitrile is about 100:0.3 to about 100:1, including about 100:0.5. Alternately, the reaction can be conducted at a first temperature ranging from about 20 to 30° C., such as about 25° C., and then cooled to a second temperature ranging from about 3 to 10° C., such as about 4° C.

A crystalline freebase can also be prepared by forming a seed crystal of a crystalline freebase (synthesized as described above), forming a crystalline freebase by contacting the ester with an inert diluent and dissolving the resulting crystalline ester to form a solution, and adding the seed crystal to the solution.

In one embodiment, the ester is typically contacted with about 5 mg/ml to about 15 mg/ml of inert diluent. Generally, this reaction is conducted at a first temperature ranging from about 50 to 70° C., such as about 60° C. The mixture is then cooled to a second temperature ranging from about 3 to 10° C., such as about 4° C. The seed crystal of a crystalline freebase of the ester is then added, followed by several heating and cooling cycles. The first heating cycle goes, for example, from about 30 to 40° C. and then to about 50° C., followed by cooling to room temperature. The second, third and forth heating cycles involve heating the sample to a temperature ranging from about 50 to 70° C., such as about 60° C., followed by cooling to room temperature. In a particular embodiment, the ester is added to water: acetonitrile (1:1) solution, followed by the addition of water and further acetonitrile. In this reaction, the ratio of milligrams of the ester to milliliters of acetonitrile and water is about 230:0.1 to about 230:0.5, including about 230:0.2.

To prepare another form of a crystalline freebase (Form II), the ester is typically contacted with about 200 mg/ml to about 100 mg/ml of inert diluent. Generally, this reaction is conducted at a temperature ranging from about 20 to 30° C., such as about 25° C. A particularly suitable inert diluent is a combination of acetonitrile and methyl t-butyl ether. In a particular embodiment, biphenyl-2-ylcarbamic acid 1-(2-{[4-(4-carbamoylpiperidin-1-ylmethyl)benzoyl]methylamino}ethyl)piperidin-4-yl ester is added to acetonitrile, followed by the addition of methyl t-butyl ether and additional acetonitrile. In this reaction, the ratio of milligrams of the ester to milliliters of acetonitrile:methyl t-butyl ether (1:2 solution) is about 200 mg/ml to about 100 mg/ml, including about 70:0.45.

Crystalline Properties

Among other advantages, it has been discovered that forming a crystalline compound of formula I is useful for purifying the compound of formula I. For example: the crystalline diphosphate salt has a purity greater than 96%, and typically greater than 98%.

As is well known in the field of powder x-ray diffraction (PXRD), relative peak heights of PXRD spectra are dependent on a number of factors relating to sample preparation and instrument geometry, while peak positions are relatively insensitive to experimental details. Thus, in one embodiment, the crystalline compounds of the invention are characterized by a PXRD pattern having certain peak positions.

In one embodiment, a crystalline diphosphate salt of the compound of formula I is characterized by a PXRD pattern having two or more diffraction peaks at 2θ values selected from 6.4±0.2, 7.6±0.2, 8.6±0.2, 13.7±0.2, 15.0±0.2, 19.4±0.2, 21.6±0.2, 22.1±0.2, 22.9±0.2, and 23.7±0.2. In one particular embodiment, this crystalline form is characterized by a PXRD pattern comprising diffraction peaks at 2θ values of 15.0±0.2, 19.4±0.2, 21.6±0.2, and 23.7±0.2. In another embodiment, a crystalline diphosphate salt is characterized by a PXRD pattern in which the peak positions are substantially in accordance with those shown in FIG. 1. Note the differences between the PXRD pattern in FIG. 1 and the PXRD pattern for the less stable diphosphate salt as depicted in FIG. 6.

In one embodiment, a crystalline monosulfate salt of the compound of formula I is characterized by a PXRD pattern having two or more diffraction peaks at 2θ values selected from 7.7±0.2, 8.4±0.2, 8.8±0.2, 12.6±0.2, 13.7±0.2, 14.1±0.2, 15.3±0.2, 16.0±0.2, 19.7±0.2, 20.6±0.2, 23.0±0.2, and 24.4±0.2. In one particular embodiment, this crystalline form is characterized by a PXRD pattern comprising diffraction peaks at 2θ values of 12.6±0.2, 19.7±0.2, 23.0±0.2, and 24.4±0.2. In another embodiment, a crystalline monosulfate salt is characterized by a PXRD pattern in which the peak positions are substantially in accordance with those shown in FIG. 8.

In one embodiment, a crystalline dioxalate salt of the compound of formula I is characterized by a PXRD pattern having two or more diffraction peaks at 2θ values selected from 7.7±0.2, 8.7±0.2, 13.5±0.2, 14.0±0.2, 14.8±0.2, 15.4±0.2, 15.8±0.2, 19.4±0.2, 22.9±0.2, 23.3±0.2, and 24.6±0.2. In one particular embodiment, this crystalline form is characterized by a PXRD pattern comprising diffraction peaks at 2θ values of 8.7±0.2, 14.0±0.2, 19.4±0.2, and 22.9±0.2. In another embodiment, a crystalline dioxalate salt is characterized by a PXRD pattern in which the peak positions are substantially in accordance with those shown in FIG. 13.

In one embodiment, a crystalline freebase (Form I) of the compound of formula I is characterized by a PXRD pattern having two or more diffraction peaks at 2θ values selected from 4.7±0.2, 9.6±0.2, 12.7±0.2, 13.7±0.2, 16.7±0.2, 17.4±0.2, 18.5±0.2, 19.4±0.2, 20.8±0.2, 21.4±0.2, 24.2±0.2, and 25.6±0.2. In one particular embodiment, this crystalline form is characterized by a PXRD pattern comprising diffraction peaks at 20 values of 4.7±0.2, 18.5±0.2, 20.8±0.2, and 25.6±0.2. In another embodiment, a crystalline freebase (Form I) is characterized by a PXRD pattern in which the peak positions are substantially in accordance with those shown in FIG. 18.

In one embodiment, a crystalline freebase (Form II) of the compound of formula I is characterized by a PXRD pattern having two or more diffraction peaks at 2θ values selected from 4.6±0.2, 9.3±0.2, 12.9±0.2, 13.6±0.2, 14.0±0.2, 14.6±0.2, 16.5±0.2, 18.6±0.2, 19.1±0.2, 20.9±0.2, 22.1±0.2, 22.7±0.2, and 25.7±0.2. In one particular embodiment, this crystalline form is characterized by a PXRD pattern comprising diffraction peaks at 2θ values of 4.6±0.2, 18.6±0.2, 22.1±0.2, and 22.7±0.2. In another embodiment, a crystalline freebase (Form II) is characterized by a PXRD pattern in which the peak positions are substantially in accordance with those shown in FIG. 23.

Figure 2:
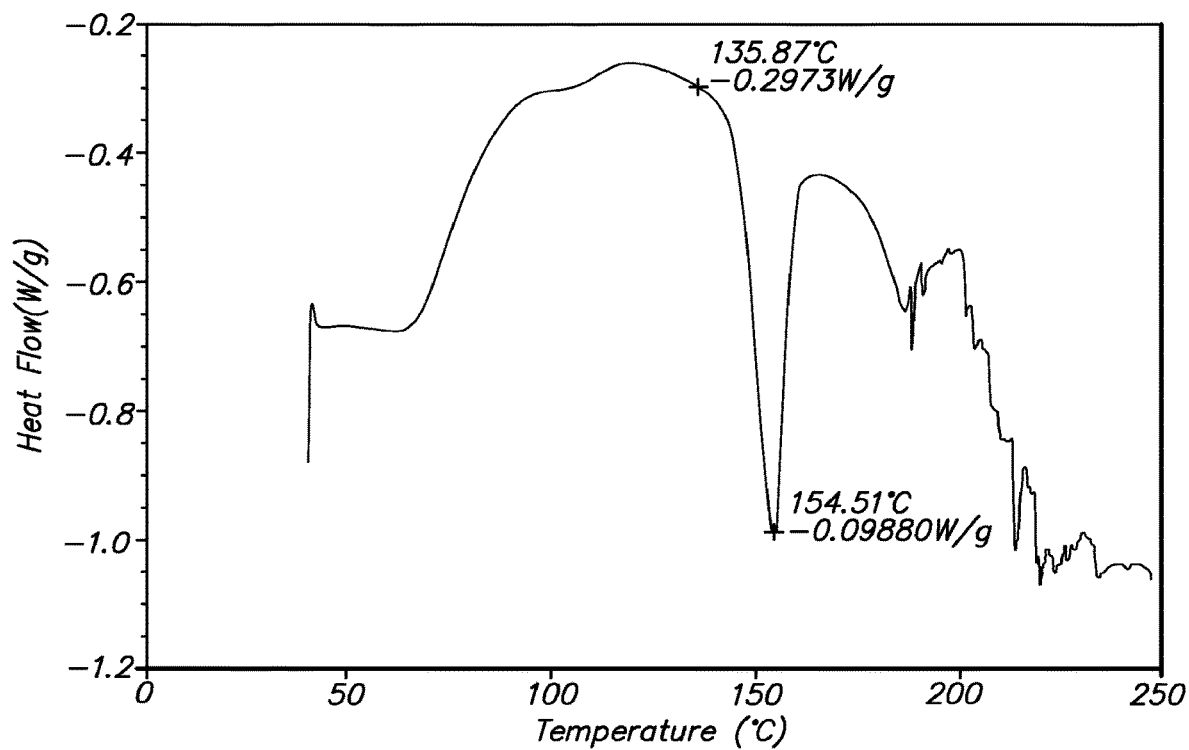
FIG. 2 shows a differential scanning calorimetry (DSC) trace for this crystalline salt.

In yet another embodiment, the crystalline compounds of formula I are characterized by their differential scanning calorimetry (DSC) trace. Thus, a crystalline diphosphate salt of the compound of formula I is characterized by its DSC trace which showed a maximum endothermic heat flow at about 154.5° C., as illustrated in FIG. 2. Note the difference between the DSC trace in FIG. 2 and the DSC trace for the less stable diphosphate salt depicted in FIG. 7. The DSC trace for the stable crystalline diphosphate salt (FIG. 2) shows a typical low temperature transition followed by a relatively sharp peak at about 154.5° C. On the other hand, the DSC trace for the unstable crystalline diphosphate salt (FIG. 7) shows a distinct shoulder prior to a much smaller melting transition at about 150.3° C.

Figure 10:
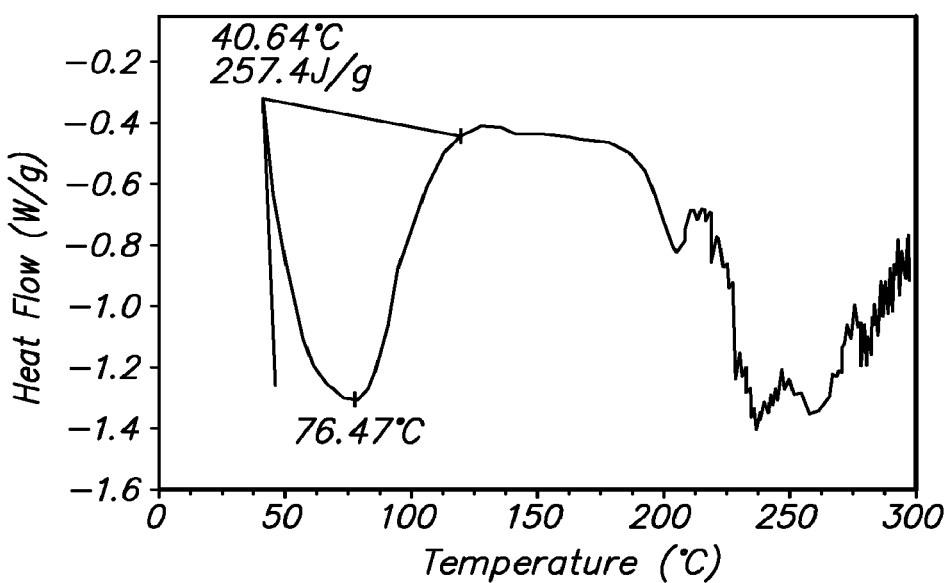
Figure 15:
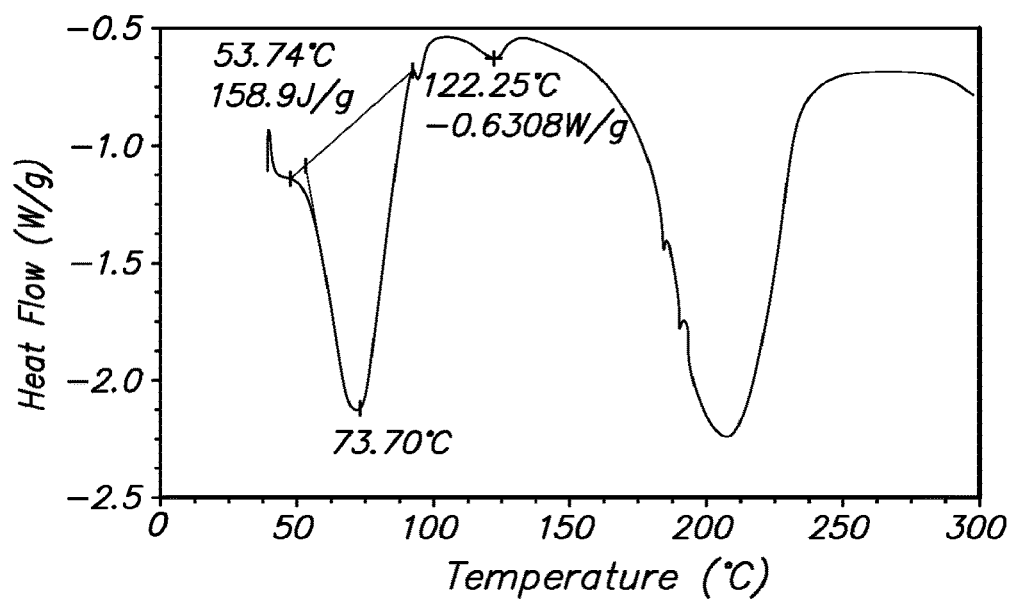
Figure 19:
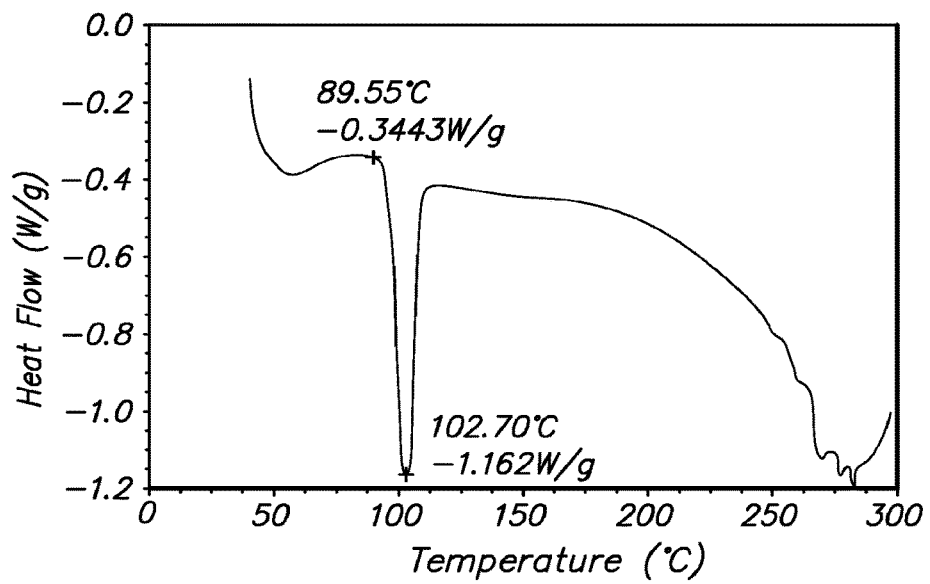
Figure 24:
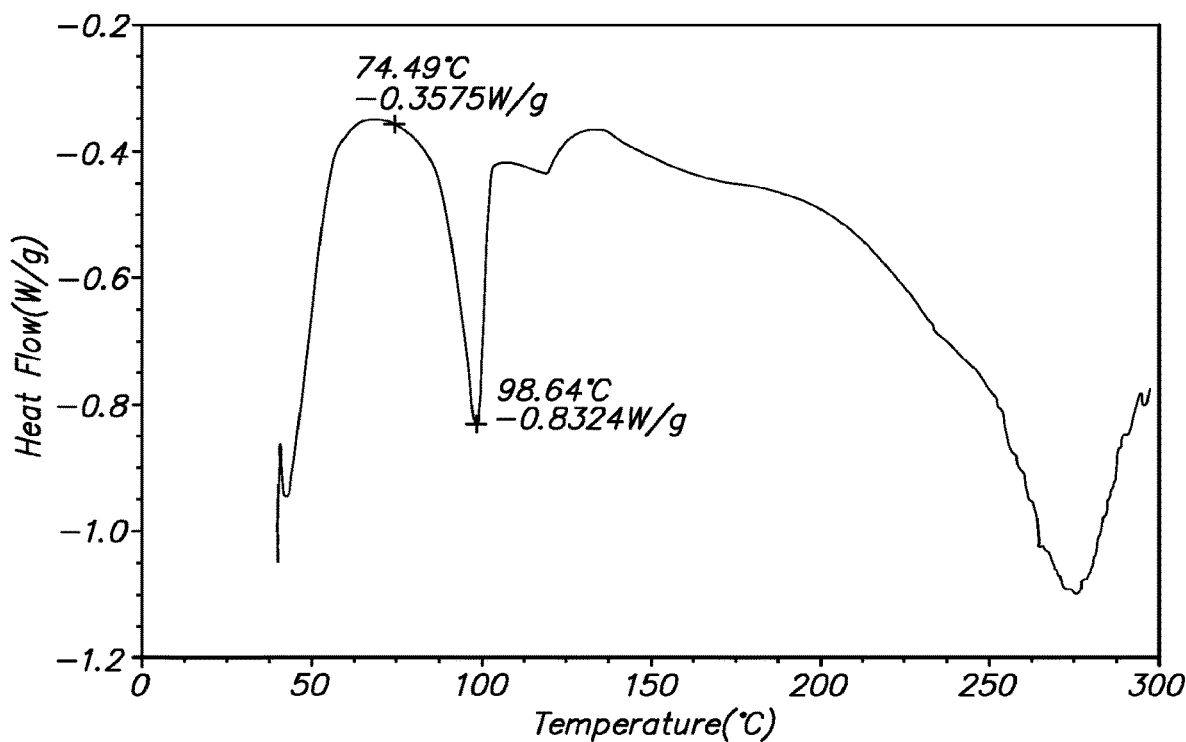

Similarly, a crystalline monosulfate salt of the compound of formula I is characterized by its DSC trace which showed a maximum endothermic heat flow at about 76.5° C., as illustrated in FIG. 10; a crystalline dioxalate salt is characterized by its DSC trace which showed a maximum endothermic heat flow at about 73.7° C., as illustrated in FIG. 15; a crystalline freebase (Form I) is characterized by its DSC trace which showed a maximum endothermic heat flow at about 102.7° C., as illustrated in FIG. 19; and a crystalline freebase (Form II) is characterized by its DSC trace which showed a maximum endothermic heat flow at about 98.6° C., as illustrated in FIG. 24.

The crystalline compounds of the invention have been demonstrated to have a reversible sorption/desorption profile with an acceptable, moderate level of hygroscopicity: a crystalline diphosphate salt of the compound of formula I exhibits less than 2% weight gain when exposed to up to 90% relative humidity; a crystalline monosulfate salt exhibits less than 4% weight gain when exposed to up to 90% relative humidity; a crystalline dioxalate salt exhibits less than 3% weight gain when exposed to up to 90% relative humidity; a crystalline freebase (Form I) exhibits less than 6% weight gain when exposed to up to 90% relative humidity; and a crystalline freebase (Form II) exhibits less than 4% weight gain when exposed to up 90% relative humidity.

Additionally, the crystalline compounds of the invention have been found to be stable upon exposure to elevated temperature and humidity. For example, after storage for 1 month at 40° C. and 75% relative humidity, analysis by high performance liquid chromatography (HPLC) showed no detectable chemical degradation (i.e., less than 0.5% degradation) for the crystalline compounds of the invention.

These properties of the crystalline compounds of the invention are further illustrated in the Examples below.

Pharmaceutical Compositions and Formulations

The crystalline compound of formula I is typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration. However, it will be understood by those skilled in the art that, once the crystalline salt of the invention has been formulated, it may no longer be in crystalline form, i.e., the salt may be dissolved in a suitable carrier.

Accordingly, in one embodiment, the invention is directed to a pharmaceutical composition comprising a pharmaceutically acceptable carrier or excipient and a crystalline biphenyl-2-ylcarbamic acid 1-(2-{[4-(4-carbamoylpiperidin-1-ylmethyl)benzoyl]methylamino}ethyl)piperidin-4-yl ester or a pharmaceutically acceptable solvate thereof. The pharmaceutical composition may contain other therapeutic and/or formulating agents if desired.

The pharmaceutical compositions of the invention typically contain a therapeutically effective amount of a crystalline biphenyl-2-ylcarbamic acid 1-(2-{[4-(4-carbamoylpiperidin-1-ylmethyl)benzoyl]methylamino}ethyl) piperidin-4-yl ester or a pharmaceutically acceptable solvate thereof, as the active agent. Typically, such pharmaceutical compositions will contain from about 0.01 to about 95% by weight of the active agent; including, from about 0.01 to about 30% by weight; such as from about 0.01 to about 10% by weight of the active agent.

Any conventional carrier or excipient may be used in the pharmaceutical compositions of the invention. The choice of a particular carrier or excipient, or combination of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts.

Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials that can serve as pharmaceutically acceptable carriers include, but are not limited to, the following: sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; compressed propellant gases such as chlorofluorocarbons and hydrofluorocarbons; and other non-toxic compatible substances employed in pharmaceutical compositions.

The pharmaceutical compositions of the invention are typically prepared by thoroughly and intimately mixing or blending a compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of the invention are suitable for inhaled administration. Suitable pharmaceutical compositions for inhaled administration will typically be in the form of an aerosol or a powder. Such compositions are generally administered using well-known delivery devices such as a nebulizer inhaler, a metered-dose inhaler (MDI), a dry powder inhaler (DPI) or a similar delivery device.

In a specific embodiment of the invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Suitable nebulizer devices are commercially available, for example, by PARI GmbH (Stamberg, German). Other nebulizer devices include Respimat (Boehringer Ingelheim) and those described, for example, in U.S. Pat. No. 6,123,068 to Lloyd et al. and WO 97/12687 (Eicher et al.), the disclosures of which are incorporated herein by reference in their entirety.

A representative pharmaceutical composition for use in a nebulizer inhaler comprises an aqueous solution comprising from about 0.05 µg/mL to about 10 mg/mL of a crystalline compound of formula I or a pharmaceutically acceptable solvate thereof. In one embodiment, the aqueous formulation is isotonic. In one embodiment, the aqueous formulation has a pH in the range of from about 4 to 6. In a particular embodiment, the aqueous formulation is buffered with citrate buffer to a pH of about 5. In another particular embodiment, the aqueous formulation contains from about 0.1 mg/mL to about 1.0 mg/mL free base equivalents of biphenyl-2-ylcarbamic acid 1-(2-{[4-(4-carbamoylpiperidin-1-ylmethyl)benzoyl]methylamino}ethyl) piperidin-4-yl ester.

In another specific embodiment of the invention, the pharmaceutical composition comprising the active agent is administered by inhalation using a DPI. Such DPIs typically administer the active agent as a free-flowing powder that is dispersed in a patient's air-stream during inspiration. In order to achieve a free flowing powder, the active agent is typically formulated with a suitable excipient such as lactose or starch. Micronization is a common method of reducing crystal size to that suitable for pulmonary delivery. Typically, the active agent is micronized and combined with a suitable carrier to form a suspension of micronized particles of respirable size, where "micronized particles" or "micronized form" means at least about 90% of the particles have a diameter of less than about 10 µm. Other methods of reducing particle size may also be used such as fine milling, chopping, crushing, grinding, milling, screening, trituration, pulverization, and so forth, as long as the desired particle size can be obtained.

A representative pharmaceutical composition for use in a DPI comprises dry lactose having a particle size between about 1 µm and about 100 µm and micronized particles of a crystalline compound of formula I, or a pharmaceutically acceptable solvate thereof. Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of DPI delivery devices include Diskhaler (GlaxoSmithKline, Research Triangle Park, N.C.; see, e.g., U.S. Pat. No. 5,035,237 to Newell et al.); Diskus (GlaxoSmithKline; see, e.g., U.S. Pat. No. 6,378,519 to Davies et al.); Turbuhaler (AstraZeneca, Wilmington, Del.; see, e.g., U.S. Pat. No. 4,524,769 to Wetterlin); Rotahaler (GlaxoSmithKline; see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S. Pat. No. 5,239,993 to Evans, and U.S. Pat. No. 5,715,810 to Armstrong et al., and references cited therein. The disclosures of the aforementioned patents are incorporated herein by reference in their entirety.

In yet another specific embodiment of the invention, the pharmaceutical composition comprising the active agent is administered by inhalation using an MDI, which typically discharges a measured amount of the active agent or a pharmaceutically acceptable salt or solvate or stereoisomer thereof using compressed propellant gas. Accordingly, pharmaceutical compositions administered using an MDI typically comprise a solution or suspension of the active agent in a liquefied propellant. Any suitable liquefied propellant may be employed including chlorofluorocarbons such as $CCl_3F$, and hydrofluoroalkanes (HFAs) such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents such as ethanol or pentane, and surfactants such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company, the disclosures of which are incorporated herein by reference in their entirety.

A representative pharmaceutical composition for use in a metered-dose inhaler comprises from about 0.01 to 5% by weight of a crystalline compound of formula I, or a pharmaceutically acceptable solvate thereof; from about 0 to 20% by weight ethanol; and from about 0 to 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are described in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.). The disclosures of the aforementioned patents and publications are incorporated herein by reference in their entirety.

For additional examples of processes of preparing respirable particles, and formulations and devices suitable for inhalation dosing see U.S. Pat. No. 6,268,533 to Gao et al., U.S. Pat. No. 5,983,956 to Trofast; U.S. Pat. No. 5,874,063 to Briggner et al.; and U.S. Pat. No. 6,221,398 to Jakupovic et al.; and WO 99/55319 (Glaxo Group Ltd.) and WO 00/30614 (AstraZeneca AB); the disclosures of which are incorporated herein by reference in their entirety.

In another embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a salt of the invention as an active ingredient. The pharmaceutical composition may be packaged in a unit dosage form.

When intended for oral administration in a solid dosage form (i.e., as capsules, tablets, pills and the like), the pharmaceutical compositions of the invention will typically comprise a crystalline compound of the present invention as the active ingredient and one or more pharmaceutically acceptable carriers such as sodium citrate or dicalcium phosphate. Optionally or alternatively, such solid dosage forms may also comprise: fillers or extenders such as starches, lactose, sucrose, glucose, mannitol, and/or silicic acid; binders such as carboxymethylcellulose, alginates, gelatin, polyvinyl pyrrolidone, sucrose and/or acacia; humectants such as glycerol; disintegrating agents such as agar-agar, calcium carbonate, potato or tapioca starch, alginic acid, certain silicates, and/or sodium carbonate; solution retarding agents such as paraffin; absorption accelerators such as quaternary ammonium compounds; wetting agents such as cetyl alcohol and/or glycerol monostearate; absorbents such as kaolin and/or bentonite clay; lubricants such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically acceptable antioxidants include: water-soluble antioxidants such as ascorbic acid, cysteine hydrochloride, sodium bisulfate, sodium metabisulfate sodium sulfite and the like; oil-soluble antioxidants such as ascorbyl palmitate, butylated hydroxyanisole (BHA), butylated hydroxytoluene (BHT), lecithin, propyl gallate, alpha-tocopherol, and the like; and metal-chelating agents such as citric acid, ethylenediamine tetraacetic acid (EDTA), sorbitol, tartaric acid, phosphoric acid, and the like. Coating agents for tablets, capsules, pills and like, include those used for enteric coatings such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, oils (especially cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The crystalline compounds of the invention can also be administered transdermally using known transdermal delivery systems and excipients. For example, a compound of the invention can be admixed with permeation enhancers such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The crystalline compounds of the invention can also be co-administered with other therapeutic agents. This combination therapy involves using a compound of the invention combined with one or more of these secondary agents, either formulated together (e.g., packaged together in a single formulation) or formulated separately (e.g., packaged as separate unit dosage forms). Methods of formulating multiple agents together in the same formulation or in separate unit dosage forms, are well known in the art.

The additional therapeutic agent(s) can be selected from other bronchodilators (e.g., $PDE_3$ inhibitors, adenosine 2b modulators and $\beta_2$ adrenergic receptor agonists); anti-inflammatory agents (e.g., steroidal anti-inflammatory agents such as corticosteroids; non-steroidal anti-inflammatory agents (NSAIDs), and $PDE_4$ inhibitors); other muscarinic receptor antagonists (i.e., antichlolinergic agents); antiinfective agents (e.g., Gram positive and Gram negative antibiotics or antivirals); antihistamines; protease inhibitors; and afferent blockers (e.g., $D_2$ agonists and neurokinin modulators).

One particular embodiment of the invention is directed to a composition comprising (a) a pharmaceutically acceptable carrier and a therapeutically effective amount of a crystalline form of the compound of formula I; and (b) a pharmaceutically acceptable carrier and a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the compound of formula I and the agent are formulated together or separately. In another embodiment, (b) is a pharmaceutically acceptable carrier and a therapeutically effective amount of a $\beta_2$ adrenergic receptor agonist and a steroidal anti-inflammatory agent. The secondary agents can be used in the form of pharmaceutically acceptable salts or solvates, and if appropriate, as optically pure stereoisomers.

Representative $\beta_2$ adrenergic receptor agonists that can be used in combination with crystalline compounds of the invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl)benzenesulfonamide and related compounds described in WO 02/066422 (Glaxo Group Ltd.); 3-[3-(4-{[6-([(2R)-2-hydroxy-2-[4-hydroxy-3-(hydroxymethyl)phenyl]ethyl}amino)hexyl]oxy}butyl)-phenyl]imidazolidine-2,4-dione and related compounds described in WO 02/070490 (Glaxo Group Ltd.); 3-(4-{[6-({(2R)-2-[3-(formylamino)-4-hydroxyphenyl]-2-hydroxyethyl}amino)hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino)hexyl]oxy}butyl)-benzenesulfonamide, N-(tert-butyl)-3-(4-

{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl) benzenesulfonamide and related compounds described in WO 02/076933 (Glaxo Group Ltd.); 4-{(1R)-2-[(6-{2-[(2,6-dichlorobenzyl)oxy]ethoxy}hexyl)amino]-1-hydroxyethyl}-2-(hydroxymethyl)phenol and related compounds described in WO 03/024439 (Glaxo Group Ltd.); N-{2-[4-((R)-2-hydroxy-2-phenylethylamino)phenyl]ethyl}-(R)-2-hydroxy-2-(3-formamido-4-hydroxyphenyl)ethylamine and related compounds described in U.S. Pat. No. 6,576,793 to Moran et al.; N-{2-[4-(3-phenyl-4-methoxy phenyl)aminophenyl]ethyl}-(R)-2-hydroxy-2-(8-hydroxy-2(1H)-quinolinon-5-yl)ethylamine and related compounds described in U.S. Pat. No. 6,653,323 to Moran et al.; and pharmaceutically acceptable salts thereof. In a particular embodiment, the $\beta_2$-adrenoreceptor agonist is a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 μg to 500 μg per dose. The disclosures of the aforementioned patents and publications are incorporated herein by reference in their entirety.

Representative steroidal anti-inflammatory agents that can be used in combination with crystalline compounds of the invention include, but are not limited to, methyl prednisolone, prednisolone, dexamethasone, fluticasone propionate, 6α,9α-difluoro-17α-[(2-furanyl carbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the composition in a therapeutically effective amount. Typically, the steroidal anti-inflammatory agent will be present in an amount sufficient to provide from about 0.05 μg to 500 μg per dose.

An exemplary combination is a crystalline form of the compound of formula I or solvate thereof, co-administered with salmeterol as the $\beta_2$ adrenergic receptor agonist, and fluticasone propionate as the steroidal anti-inflammatory agent. Another exemplary combination is a crystalline form of the compound of formula I or solvate thereof, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl) ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent. As noted above, these agents can be formulated together or separately.

Other suitable combinations include, for example, other anti-inflammatory agents, e.g., NSAIDs (e.g., sodium cromoglycate, nedocromil sodium, and phosphodiesterase (PDE) inhibitors such as theophylline, PDE4 inhibitors and mixed PDE3/PDE4 inhibitors); leukotriene antagonists (e.g., monteleukast); inhibitors of leukotriene synthesis; iNOS inhibitors; protease inhibitors such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

Representative phosphodiesterase-4 (PDE4) inhibitors or mixed PDE3/PDE4 inhibitors that can be used in combination with the crystalline compounds of the invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl) cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds described in WO99/16766 (Kyowa Hakko); K-34 (Kyowa Hakko); V-11294A (Napp); roflumilast (Byk-Gulden); pthalazinone compounds described in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with the crystalline compounds of the invention include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the crystalline compounds of the invention include, but are not limited to, ethanolamines such as carbinoxamine maleate, clemastine fumarate, diphenylhydramine hydrochloride and dimenhydrinate; ethylenediamines such as pyrilamine amleate, tripelennamine hydrochloride and tripelennamine citrate; alkylamines such as chlorpheniramine and acrivastine; piperazines such as hydroxyzine hydrochloride, hydroxyzine pamoate, cyclizine hydrochloride, cyclizine lactate, meclizine hydrochloride and cetirizine hydrochloride; piperidines such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Unless otherwise indicated, exemplary suitable doses for the other therapeutic agents administered in combination with a crystalline compound of the invention are in the range of about 0.05 µg/day to 100 mg/day.

The following formulations illustrate representative pharmaceutical compositions of the invention, as well as exemplary methods of preparation. One or more secondary agents can optionally be formulated with the crystalline compound of the invention (primary active agent). Alternately, the secondary agents(s) can be formulated separately and co-administered with the primary active agent, either simultaneously or sequentially. For example, in one embodiment, a single dry powder formulation can be manufactured to include both the crystalline compound of the invention and one or more secondary agents. In another embodiment, one formulation is manufactured to contain the crystalline compound of the invention and separate formulation(s) are manufactured to contain the secondary agent(s). Such dry powder formulations can then be packaged in separate blister packs and administered with a single DPI device.

Exemplary Dry Powder Formulation for Administration by Inhalation 0.2 mg of a crystalline compound of the invention is micronized and then blended with 25 mg of lactose. The blended mixture is then loaded into a gelatin inhalation cartridge. The contents of the cartridge are administered using a powder inhaler.

Exemplary Dry Powder Formulation for Administration by a Dry Powder Inhaler

A dry powder is prepared having a bulk formulation ratio of micronized crystalline compound of the invention (active agent) to lactose of 1:200. The powder is packed into a dry powder inhalation device capable of delivering between about 10 µg and 100 µg of active agent per dose.

Exemplary Formulations for Administration by a Metered Dose Inhaler

A suspension containing 5 wt % of a crystalline compound of the invention (active agent) and 0.1 wt % lecithin is prepared by dispersing 10 g of the active agent as micronized particles with a mean size less than 10 µm in a solution formed from 0.2 g of lecithin dissolved in 200 mL of demineralized water. The suspension is spray dried and the resulting material is micronized to particles having a mean diameter less than 1.5 µm. The particles are loaded into cartridges with pressurized 1,1,1,2-tetrafluoroethane.

Alternately, a suspension containing 5 wt % of the active agent, 0.5 wt % lecithin, and 0.5 wt % trehalose is prepared by dispersing 5 g of the active agent as micronized particles with a mean size less than 10 µm in a colloidal solution formed from 0.5 g of trehalose and 0.5 g of lecithin dissolved in 100 mL of demineralized water. The suspension is spray dried and the resulting material is micronized to particles having a mean diameter less than 1.5 µm. The particles are loaded into canisters with pressurized 1,1,1,2-tetrafluoroethane.

Exemplary Aqueous Aerosol Formulation for Administration by Nebulizer

A pharmaceutical composition is prepared by dissolving 0.5 mg of a crystalline compound of the invention (active agent) in 1 mL of a 0.9% sodium chloride solution acidified with citric acid. The mixture is stirred and sonicated until the active agent is dissolved. The pH of the solution is adjusted to a value in the range of from 3 to 8 (typically about 5) by the slow addition of NaOH.

Exemplary Hard Gelatin Capsule Formulation for Oral Administration

The following ingredients are thoroughly blended and then loaded into a hard gelatin capsule: 250 mg of a crystalline compound of the invention, 200 mg of lactose (spray-dried), and 10 mg of magnesium stearate, for a total of 460 mg of composition per capsule.

Exemplary Suspension Formulation for Oral Administration

The following ingredients are mixed to form a suspension containing 100 mg of active ingredient per 10 mL of suspension.

| Ingredients | Amount |
| --- | --- |
| Crystalline compound of the invention | 1.0 g |
| Fumaric acid | 0.5 g |
| Sodium chloride | 2.0 g |
| Methyl paraben | 0.15 g |
| Propyl paraben | 0.05 g |

| Ingredients | Amount |
| --- | --- |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Exemplary Injectable Formulation

The following ingredients are blended and the pH is adjusted to 4±0.5 using 0.5 N HCl or 0.5 N NaOH.

| Ingredients | Amount |
| --- | --- |
| Crystalline compound of the invention | 0.2 g |
| Sodium acetate buffer solution (0.4M) | 2.0 mL |
| HCl (0.5N) or NaOH (0.5N) | q.s. to pH 4 |
| Water (distilled, sterile) | q.s. to 20 mL |

Utility

The compound of formula I possesses muscarinic receptor antagonist activity and therefore, the crystalline form of the compound of formula I is expected to be useful for treating medical conditions mediated by muscarinic receptors, i.e., medical conditions that are ameliorated by treatment with a muscarinic receptor antagonist. Such medical conditions include, by way of example, pulmonary disorders or diseases including those associated with reversible airway obstruction such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders such as overactive bladder or detrusor hyperactivity and their symptoms; gastrointestinal tract disorders such as irritable bowel syndrome, diverticular disease, achalasia, gastrointestinal hypermotility disorders and diarrhea; cardiac arrhythmias such as sinus bradycardia; Parkinson's disease; cognitive disorders such as Alzheimer's disease; dismenorrhea; and the like.

Accordingly, in one embodiment, the invention is directed to a method for treating a pulmonary disorder, the method comprising administering to a patient a therapeutically effective amount of a crystalline biphenyl-2-ylcarbamic acid 1-(2-{[4-(4-carbamoyl piperidin-1-ylmethyl)benzoyl]methylamino}ethyl)piperidin-4-yl ester or a pharmaceutically acceptable solvate thereof. When used to treat a pulmonary disorder, the crystalline compound of the invention will typically be administered by inhalation in multiple doses per day, in a single daily dose or a single weekly dose. Generally, the dose for treating a pulmonary disorder will range from about 10 µg/day to 200 µg/day.

When administered by inhalation, the crystalline compounds of the invention typically have the effect of producing bronchodilation. Accordingly, in another embodiment, the invention is directed to a method of producing bronchodilation in a patient, the method comprising administering to a patient a bronchodilation-producing amount of a crystalline biphenyl-2-ylcarbamic acid 1-(2-{[4-(4-carbamoylpiperidin-1-ylmethyl)benzoyl]methylamino}ethyl)piperidin-4-yl ester or a pharmaceutically acceptable solvate thereof. Generally, the therapeutically effective dose for producing bronchodilation will range from about 10 µg/day to 200 µg/day.

In one embodiment, the invention is directed to a method of treating chronic obstructive pulmonary disease or asthma, the method comprising administering to a patient a therapeutically effective amount of a crystalline biphenyl-2-ylcarbamic acid 1-(2-{[4-(4-carbamoylpiperidin-1-ylmethyl)benzoyl]methylamino}ethyl)piperidin-4-yl ester or a pharmaceutically acceptable solvate thereof. When used to treat a COPD or asthma, the salt of the invention will typically be administered by inhalation in multiple doses per day or in a single daily dose. Generally, the dose for treating COPD or asthma will range from about 10 µg/day to 200 µg/day. As used herein, COPD includes chronic obstructive bronchitis and emphysema (see, for example, Barnes, Chronic Obstructive Pulmonary Disease, *N Engl J Med* 343:269-78 (2000)).

When used to treat a pulmonary disorder, the crystalline compounds of the invention are optionally administered in combination with other therapeutic agents. Accordingly, in a particular embodiment, the pharmaceutical compositions and methods of the invention further comprise a therapeutically effective amount of a $\beta_2$-adrenoreceptor agonist, a corticosteroid, a non-steroidal anti-inflammatory agent, or combination thereof.

In another embodiment, the crystalline compounds of the invention are used to antagonize a muscarinic receptor in biological system, and a mammal in particular such as mice, rats, guinea pigs, rabbits, dogs, pigs, humans and so forth. In this embodiment, a therapeutically effective amount of a crystalline compound of formula I is administered to the mammal. If desired, the effects of antagonizing the muscarinic receptor can then determined using conventional procedures and equipment.

The properties and utility of the crystalline compounds of the invention can be demonstrated using various in vitro and in vivo assays that are well-known to those skilled in the art. For example, representative assays are described in further detail in the following Examples.

EXAMPLES

The following Preparations and Examples are provided to illustrate specific embodiments of the invention. These specific embodiments, however, are not intended to limit the scope of the invention in any way unless specifically indicated. The following abbreviations have the following meanings unless otherwise indicated and any other abbreviations used herein and not defined have their standard meaning:

AC adenylyl cyclase
ACh acetylcholine
ACN acetonitrile
BSA bovine serum albumin
cAMP 3'-5' cyclic adenosine monophosphate
CHO Chinese hamster ovary
$cM_5$ cloned chimpanzee M5 receptor
DCM dichloromethane (i.e., methylene chloride)
DIPEA N,N-diisopropylethylamine
dPBS Dulbecco's phosphate buffered saline
DMSO dimethyl sulfoxide
EDC 1-ethyl-3-(3-dimethylaminopropyl)carbodiimide
EDTA ethylenediaminetetraacetic acid
FBS fetal bovine serum
FLIPR fluorometric imaging plate reader
HBSS Hank's buffered salt solution
HEPES 4-(2-hydroxyethyl)-1-piperazineethanesulfonic acid
$hM_1$ cloned human M1 receptor
$hM_2$ cloned human M2 receptor
$hM_3$ cloned human M3 receptor
$hM_4$ cloned human M4 receptor
$hM_5$ cloned human M5 receptor
HOBT N-hydroxybenzotriazole
HPLC high-performance liquid chromatography
IPA isopropanol
MCh methylcholine
MTBE methyl t-butyl ether
TFA trifluoroacetic acid Any other abbreviations used herein but not defined have their standard, generally accepted meaning. Unless noted otherwise, reagents, starting materials and solvents were purchased from commercial suppliers (such as Sigma-Aldrich, Fluka, and the like) and were used without further purification.

Unless otherwise indicated, HPLC analysis was conducted using an Agilent (Palo Alto, Calif.) Series 1100 instrument equipped with a Zorbax Bonus RP 2.1×50 mm column (Agilent) having a 3.5 micron particle size. Detection was by UV absorbance at 214 nm. The mobile phases employed were as follows (by volume): A is ACN (2%), water (98%) and TFA (0.1%); and B is acetonitrile (90%), water (10%) and TFA (0.1%). HPLC 10-70 data was obtained using a flow rate of 0.5 mL/minute of 10 to 70% B over a 6 minute gradient (with the remainder being A). Similarly, HPLC 5-35 data and HPLC 10-90 data were obtained using 5 to 35% B; or 10 to 90% B over a 5 minute gradient.

Liquid chromatography mass spectrometry (LCMS) data were obtained with an Applied Biosystems (Foster City, Calif.) Model API-150EX instrument. LCMS 10-90 data was obtained using 10 to 90% Mobile Phase B over a 5 minute gradient.

Preparation 1

Biphenyl-2-ylcarbamic Acid Piperidin-4-yl Ester

Biphenyl-2-isocyanate (97.5 g, 521 mmol) and 4-hydroxy-N-benzylpiperidine (105 g, 549 mmol) were heated together at 70° C. for 12 hours. The reaction mixture was then cooled to 50° C. and ethanol (1 L) was added and then 6M HCl (191 mL) was added slowly. The resulting mixture was then cooled to ambient temperature and ammonium formate (98.5 g, 1.56 mol) was added and then nitrogen gas was bubbled through the solution vigorously for 20 minutes. Palladium on activated carbon (20 g, 10 wt % dry basis) was then added and the reaction mixture was heated at 40° C. for 12 hours, and then filtered through a pad of Celite. The solvent was then removed under reduced pressure and 1M HCl (40 mL) was added to the crude residue. The pH of the mixture was then adjusted with 10 N NaOH to pH 12. The aqueous layer was extracted with ethyl acetate (2×150 mL) and the organic layer was dried (magnesium sulfate), filtered and the solvent removed under reduced pressure to give 155 g of the title intermediate (100% yield). HPLC (10-70) $R_f$=2.52; m/z: [M+H$^+$] calc'd for $C_{18}H_{20}N_2O_2$ 297.15; found 297.3.

Preparation 2

N-Benzyl-N-methylaminoacetaldehyde

To a 3-necked 2-L flask was added N-benzyl-N-methyl-ethanolamine (30.5 g, 0.182 mol), DCM (0.5 L), DIPEA (95 mL, 0.546 mol) and DMSO (41 mL, 0.728 mol). Using an ice bath, the mixture was cooled to about −10° C. and sulfur trioxide pyridine-complex (87 g, 0.546 mol) was added in 4 portions over 5 minute intervals. The reaction was stirred at −10° C. for 2 hours. Before removing the ice-bath, the reaction was quenched by adding water (0.5 L). The aqueous layer was separated and the organic layer was washed with water (0.5 L) and brine (0.5 L) and then dried over magnesium sulfate and filtered to provide the title compound which was used without further purification.

Preparation 3

Biphenyl-2-ylcarbamic Acid 1-[2-(Benzylmethyl-amino)ethyl]piperidin-4-yl Ester

To a 2-L flask, containing the product of Preparation 2 in DCM (0.5 L) was added the product of Preparation 1 (30 g, 0.101 mol) followed by sodium triacetoxyborohydride (45 g, 0.202 mol). The reaction mixture was stirred overnight and then quenched by the addition of 1 N hydrochloric acid (0.5 L) with vigorous stirring. Three layers were observed and the aqueous layer was removed. After washing with 1N NaOH (0.5 L), a homogenous organic layer was obtained which was then washed with a saturated solution of aqueous NaCl (0.5 L), dried over magnesium sulfate, filtered and the solvent removed under reduced pressure. The residue was purified by dissolving it in a minimal amount of isopropanol and cooling this solution to 0° C. to form a solid which was collected and washed with cool isopropanol to provide 42.6 g of the title compound (95% yield). MS m/z: [M+H$^+$] calc'd f for $C_{28}H_{33}N_3O_2$ 444.3; found 444.6. $R_f$=3.51 min (10-70 ACN:H$_2$O, reverse phase HPLC).

Preparation 3A

Biphenyl-2-ylcarbamic Acid 1-[2-(Benzylmethyl-amino)ethyl]piperidin-4-yl Ester

The title compound was prepared by mesylation of N-benzyl-N-methyl ethanolamine, which was then reacted with biphenyl-2-ylcarbamic acid piperidin-4-yl ester in an alkylation reaction.

A 500 mL flask (reactor flask) was charged with N-benzyl-N-methylethanolamine (24.5 mL), DCM (120 mL), NaOH (80 mL; 30 wt %) and tetrabutylammonium chloride. Mixing at low speed throughout the reaction, the mixture was cooled to −10° C. (cooling bath), and the addition funnel charged with DCM (30 mL) and mesyl chloride (15.85 mL), which was added drop wise at a constant rate over 30 minutes. The addition was exothermic, and stirring was continued for 15 minutes while the temperature equilibrated back to −10° C. The reaction was held for at least 10 minutes to ensure full hydrolysis of the excess mesyl chloride.

A 250 mL flask was charged with biphenyl-2-ylcarbamic acid piperidin-4-yl ester (26 g; prepared as described in Preparation 1) and DCM (125 mL), stirred for 15 minutes at room temperature, and the mixture chilled briefly to 10° C. to form a slurry. The slurry was then charged into the reactor flask via the addition funnel. The cooling bath was removed and the reaction mixture was warmed to 5° C. The mixture was transferred to a separatory funnel, the layers allowed to settle, and the aqueous layer removed. The organic layer was transferred back to the reactor flask, stirring resumed, the mixture held to room temperature, and the reaction monitored by HPLC for a total of 3.5 hours.

The reactor flask was charged with NaOH (1M solution; 100 mL), stirred, and the layers allowed to settle. The organic layer was separated, washed (NaCl satd. solution), its volume partially reduced under vacuum, and subjected to repeated IPA washings. The solids were collected and allowed to air-dry (25.85 g, 98% purity). Additional solids were obtained from further processing of the mother liquor (volume reduction, IPA, cooling).

Preparation 4

Biphenyl-2-ylcarbamic Acid 1-(2-Methylaminoethyl)piperidin-4-yl Ester

To a Parr hydrogenation flask was added the product of Preparation 3 (40 g, 0.09 mol) and ethanol (0.5 L). The flask was flushed with nitrogen gas and palladium on activated carbon (15 g, 10 wt % (dry basis), 37% wt/wt) was added along with acetic acid (20 mL). The mixture was kept on the Parr hydrogenator under a hydrogen atmosphere (~50 psi) for 3 hours. The mixture was then filtered and washed with ethanol. The filtrate was condensed and the residue was dissolved in a minimal amount of DCM. Isopropyl acetate (10 volumes) was added slowly to form a solid which was collected to provide 22.0 g of the title compound (70% yield). MS m/z: [M+H$^+$] calc'd for $C_{21}H_{27}N_3O_2$ 354.2; found 354.3. $R_f$=2.96 min (10-70 ACN:H$_2$O, reverse phase HPLC).

Preparation 5

Biphenyl-2-ylcarbamic Acid 1-{2-[(4-Formylbenzoyl)methylamino]ethyl}piperidin-4-yl Ester To a three-necked 1-L flask was added 4-carboxybenzaldehyde (4.77 g, 31.8 mmol), EDC (6.64 g, 34.7 mmol), HOBT (1.91 g, 31.8 mmol), and DCM (200 mL). When the mixture was homogenous, a solution of the product of Preparation 4 (10 g, 31.8 mmol) in DCM (100 mL) was added slowly. The reaction mixture was stirred at room temperature for approximately 16 hours and then washed with water (1×100 mL), 1N HCl (5×60 mL), 1N NaOH (1×100 mL) brine (1×50 mL), dried over sodium sulfate, filtered and concentrated to afford 12.6 g of the title compound (92% yield; 85% purity based on HPLC). MS m/z:

[M+H+] calc'd for $C_{29}H_{31}N_3O_4$ 486.2; found 486.4. $R_f$ ⊂ 3.12 min (10-70 ACN:H$_2$O, reverse phase HPLC).

Example 1

Biphenyl-2-ylcarbamic Acid 1-(2-{[4-(4-Carbamoylpiperidin-1-ylmethyl)benzoyl]methylamino}ethyl)piperidin-4-yl Ester

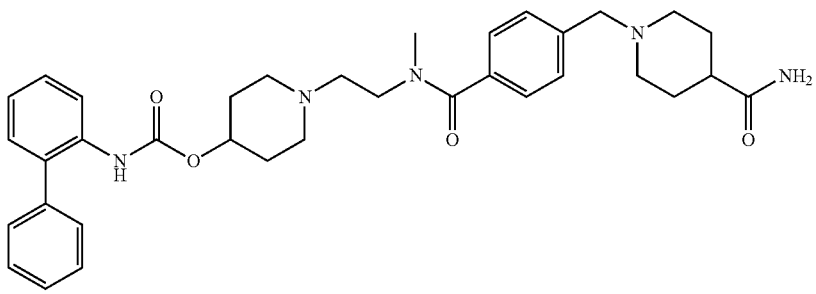 [SMILES: CN(CCN1CCC(OC(=O)Nc2ccccc2-c2ccccc2)CC1)C(=O)c1ccc(CN2CCC(C(N)=O)CC2)cc1]

To a three-necked 2-L flask was added isonipecotamide (5.99 g, 40.0 mmol), acetic acid (2.57 mL), sodium sulfate (6.44 g) and isopropanol (400 mL). The reaction mixture was cooled to 0-10° C. with an ice bath and a solution of biphenyl-2-ylcarbamic acid 1-{2-[(4-formylbenzoyl)methylamino]ethyl}piperidin-4-yl ester (11 g, 22.7 mmol; prepared as described in Preparation 5) in isopropanol (300 mL) was slowly added. The reaction mixture was stirred at room temperature for 2 hours and then cooled to 0-10° C. Sodium triacetoxyborohydride (15.16 g, 68.5 mmol) was added portion wise and this mixture was stirred at room temperature for 16 hours. The reaction mixture was then concentrated under reduced pressure to a volume of about 50 mL and this mixture was acidified with 1N HCl (200 mL) to pH 3. The resulting mixture was stirred at room temperature for 1 hour and then extracted with DCM (3×250 mL). The aqueous phase was then cooled to 0-5° C. with an ice bath and 50% aqueous NaOH solution was added to adjust the pH of the mixture to 10. This mixture was then extracted with isopropyl acetate (3×300 mL) and the combined organic layers were washed with water (100 mL), brine (2×50 mL), dried over sodium sulfate, filtered and concentrated to afford 10.8 g of the title compound (80% yield). MS m/z: [M+H+] calc'd for $C_{35}H_{43}N_5O_4$ 598.3; found 598.6. $R_f$ ⊂ 2.32 min (10-70 ACN:H$_2$O, reverse phase HPLC).

Example 2

Crystalline Diphosphate Salt of Biphenyl-2-ylcarbamic Acid 1-(2-{[4-(4-Carbamoylpiperidin-1-ylmethyl)benzoyl]methylamino}ethyl)piperidin-4-yl Ester 500 mg of biphenyl-2-ylcarbamic acid 1-(2-{[4-(4-carbamoylpiperidin-1-ylmethyl) benzoyl]methylamino}ethyl)piperidin-4-yl ester (0.826 mmol of 96% pure material; prepared as described in Example 1) was taken up in 5 ml of water and 1.5 ml of 1M phosphoric acid. The pH was adjusted to approximately pH 5.3 with an additional 0.25 ml of 1M phosphoric acid (equaling 2.1 molar equivalents). The clear solution was filtered through a 0.2 micron filter, frozen and lyophilized to dryness to yield an amorphous diphosphate salt.

20 mg of the amorphous diphosphate salt was dissolved in 2 ml of IPA:ACN (1:1). 0.1 ml of water was added and the mixture heated to 60° C. under stirring. Almost all of the solids dissolved. The suspension was allowed to cool to ambient temperature, under stirring, overnight. The resulting crystals were collected by filtration and air-dried for 20 minutes to give the title compound (18.5 mg, 93% yield) as a white crystalline solid. When examined under a microscope using polarized light, the crystals exhibited some birefringence.

Example 3

Crystalline Diphosphate Salt of Biphenyl-2-ylcarbamic Acid 1-(2-{[4-(4-Carbamoylpiperidin-1-ylmethyl)benzoyl]methylamino}ethyl)piperidin-4-yl Ester 5.0 g of biphenyl-2-ylcarbamic acid 1-(2-{[4-(4-carbamoylpiperidin-1-ylmethyl)benzoyl]methylamino}ethyl)piperidin-4-yl ester (freebase; prepared as described in Example 1) was combined with 80 ml of IPA:ACN (1:1). 4.0 ml of water was added and the mixture heated to 50° C. under stirring, forming a clear solution. To this was added dropwise at 50° C., 16 ml 1M phosphoric acid. The resulting cloudy solution was stirred at 50° C. for 5 hours, then allowed to cool to ambient temperature, under slow stirring, overnight. The resulting crystals were collected by filtration and air-dried for 1 hour, then under vacuum for 18 hours, to give the title compound (5.8 g, 75% yield) as a white crystalline solid (98.3% purity by HPLC).

Example 4

Crystalline Monosulfate Salt of Biphenyl-2-ylcarbamic Acid 1-(2-{[4-(4-Carbamoylpiperidin-1-ylmethyl)benzoyl]methylamino}ethyl)piperidin-4-yl Ester 442 mg of biphenyl-2-ylcarbamic acid 1-(2-{[4-(4-Carbamoylpiperidin-1-ylmethyl) benzoyl]methylamino}ethyl) piperidin-4-yl ester (0.739 mmol of 96% pure material; prepared as described in Example 1) was taken up in 5 ml of H$_2$O:ACN (1:1) and 1.45 ml of 1N sulfuric acid was added slowly, while monitoring the pH. The pH was adjusted to approx. pH 3.3. The clear solution was filtered through a 0.2 micron filter, frozen and lyophilized to dryness to yield a monosulfate salt.

30.3 mg of the monosulfate salt was dissolved in 1.65 ml of IPA:ACN (10:1). The suspension was heated by placing the vial in a pre-heated 60° C. water bath for 30 minutes. A viscous material was formed and the heat increased to 70° C. for 30 minutes. Since the material remained viscous, the heat was lowered to 60° C. and the mixture heated for an additional hour. The heat was turned off and the mixture was allowed to cool to room temperature. After 4 days, the material appeared to be solid, and the sample was allowed to sit for an additional nine days. The solid was then filtered and dried using a vacuum pump for 1 hour to give the title compound (23 mg, 76% yield).

Example 5

Crystalline Monosulfate Salt of Biphenyl-2-ylcarbamic Acid 1-(2-{[4-(4-Carbamoylpiperidin-1-ylmethyl)benzoyl]methylamino}ethyl)piperidin-4-yl Ester 161 mg of the monosulfate salt (prepared as described in Example 4) was dissolved in 8.77 ml of IPA:ACN (10:1). The suspension was heated by placing the vial in a pre-heated 70° C. water bath for 1.5 hours. Oil droplets formed within 5 minutes. The heat was lowered to 60° C. and the mixture heated for an additional 1.5 hours, followed by heating at 50° C. for 40 minutes, at 40° C. for 40 minutes, then at 30° C. for 45 minutes. The heat was turned off and the mixture was allowed to slowly cool to room temperature. The next day, the material was viewed under a microscope and indicated needles and plates. The material was then heated at 40° C. for 2 hours, at 35° C. for 30 minutes, and then at 30° C. for 30 minutes. The heat was turned off and the mixture was allowed to slowly cool to room temperature. The solid was then filtered and dried using a vacuum pump for 1 hour to give the title compound (117 mg, 73% yield).

Example 6

Crystalline Dioxalate Salt of Biphenyl-2-ylcarbamic Acid 1-(2-{[4-(4-carbamoylpiperidin-1-ylmethyl)benzoyl]methylamino}ethyl)piperidin-4-yl Ester 510 mg of biphenyl-2-ylcarbamic acid 1-(2-{[4-(4-carbamoylpiperidin-1-ylmethyl)benzoyl]methylamino}ethyl) piperidin-4-yl ester (0.853 mmol of 96% pure material; prepared as described in Example 1) was taken up in 5 ml of $H_2O$:ACN (1:1) and 1.7 ml of 1M aqueous oxalic acid was added slowly, while monitoring the pH. The pH was adjusted to approx. pH 3.0. The clear solution was filtered through a 0.2 micron filter, frozen and lyophilized to dryness to yield a dioxalate salt.

31.5 mg of the dioxalate salt was dissolved in 2.76 ml of 94% IPA/6% $H_2O$. The mixture was stirred in a pre-heated 60° C. water bath for 2.5 hours. After 25 minutes, all of the sample was in solution. The heat was turned off and the mixture was allowed to cool to room temperature. The next day, a small amount of viscous material was present. The vial was refrigerated at 4° C. After 4 days, the viscous material was still present. The vial was then placed at room temperature and observed one month later. The material appeared to be solid, and was observed to be crystalline under a microscope. The solid was then filtered and dried using a vacuum pump for 1 hour to give the title compound (20 mg, 63.5% yield).

Example 7

Crystalline Dioxalate Salt of Biphenyl-2-ylcarbamic Acid 1-(2-{[4-(4-Carbamoylpiperidin-1-ylmethyl)benzoyl]methylamino}ethyl)piperidin-4-yl Ester 150 mg of the dioxalate salt (prepared as described in Example 6) was dissolved in 13.1 ml of 94% IPA/6% $H_2O$. The mixture was stirred in a pre-heated 60° C. water bath for 2.5 hours. The heat was turned off and the mixture was allowed to cool to room temperature. The vial was refrigerated at 4° C. After 6 days, an oily material was observed with what appeared to be a crystal on the side of the vial. The vial was then allowed to reach room temperature, at which point seeds (crystalline material from Example 6) were added and allowed to sit for 16 days. During this time, more crystals were observed to come out of solution. The solid was then filtered and dried using a vacuum pump for 14 hours to give the title compound (105 mg, 70% yield).

Example 8

Crystalline Freebase Biphenyl-2-ylcarbamic Acid 1-(2-{[4-(4-Carbamoylpiperidin-1-ylmethyl)benzoyl]methylamino}ethyl)piperidin-4-yl Ester (Form I)

109 mg of biphenyl-2-ylcarbamic acid 1-(2-{[4-(4-carbamoylpiperidin-1-ylmethyl)benzoyl]methylamino}ethyl) piperidin-4-yl ester (prepared as described in Example 1) was dissolved in 0.56 ml of $H_2O$:ACN (1:1). The suspension was left in a vial (cap loosely placed on top) to allow for a slower evaporation time. The vial was placed under a nitrogen flow environment, although the nitrogen was not used for evaporation, only for the environment. A precipitate was visible within 1 day, which was observed to be crystalline under a microscope. The solid was then placed on a high vacuum line to remove all solvent to give the title compound. Quantitative recovery, 97.8% pure by HPLC.

In an alternate procedure, after dissolving in $H_2O$:ACN (1:1) (approximately 350 mg/mL), the vial was stored at 5° C., and the precipitate was visible at day 2. The solid was filtered, rinsed with water, and dried on high vacuum overnight. Recovery was 55%, with the solid having 98.2% purity and the liquid having 92.8% purity.

Example 9

Crystalline Freebase Biphenyl-2-ylcarbamic Acid 1-(2-{[4-(4-Carbamoylpiperidin-1-ylmethyl)benzoyl]methylamino}ethyl)piperidin-4-yl Ester (Form I)

50.4 mg of biphenyl-2-ylcarbamic acid 1-(2-{[4-(4-carbamoylpiperidin-1-ylmethyl)benzoyl]methylamino}ethyl) piperidin-4-yl ester (prepared as described in Example 1) was dissolved in 0.144 ml of $H_2O$:ACN (1:1). The suspension was left in vial (cap loosely placed on top) to allow for a slower evaporation time. The vial was refrigerated at 4° C. for 6 days. A precipitate was visible after 2 days. The solid was filtered and placed on a high vacuum line to remove all solvent and give the title compound as a white solid (27.8 mg, 55.2% yield).

Example 10

Crystalline Freebase Biphenyl-2-ylcarbamic Acid 1-(2-{[4-(4-Carbamoylpiperidin-1-ylmethyl)benzoyl]methylamino}ethyl)piperidin-4-yl Ester (Form I)

230 mg of biphenyl-2-ylcarbamic acid 1-(2-{[4-(4-carbamoylpiperidin-1-ylmethyl)benzoyl]methylamino}ethyl) piperidin-4-yl ester (prepared as described in Example 1) was dissolved in 0.2 ml of $H_2O$:ACN (1:1), using slight heat. The mixture was then heated in a 70° C. water bath for 2 hours. The heat was turned off and the mixture was allowed to cool to room temperature, then refrigerated at 4° C. for 1 hour. 50 µl of water was then added (oiled out), followed by the addition of 40 µl of ACN to get the sample back into solution. Seeds (crystalline material from Example 8) were added under slow stirring at room temperature. Crystals started to form, and the mixture was allowed to sit overnight, with slow stirring. The next day, a heat cool cycle was applied (30° C. for 10 minutes, 40° C. for 10 minutes, then 50° C. for 20 minutes). The heat was turned off and the mixture allowed to cool overnight, with slow stirring. The next day, a second heat/cool cycle was applied (60° C. for 1 hour, with dissolving observed at 70° C.). The heat was turned off and the mixture allowed to cool overnight, with slow stirring. The next day, crystals were present and a third heat cool cycle was applied (60° C. for 3 hours). The heat was turned off and the mixture allowed to cool overnight, with slow stirring. The next day, a heat cool cycle was applied (60° C. for 3 hours, slow cool, then 60° C. for 3 hours). The heat was turned off and the mixture allowed to cool overnight, with slow stirring. After 3 days, the solid was filtered and placed on a high vacuum line to remove all solvent and give the title compound.

Example 11

Crystalline Freebase Biphenyl-2-ylcarbamic Acid 1-(2-{[4-(4-Carbamoylpiperidin-1-ylmethyl)benzoyl]methylamino}ethyl)piperidin-4-yl Ester (Form II)

70 mg of biphenyl-2-ylcarbamic acid 1-(2-{[4-(4-carbamoylpiperidin-1-ylmethyl)benzoyl]methylamino}ethyl)piperidin-4-yl ester (prepared as described in Example 1) was dissolved in 0.1 mL ACN. After addition of 0.3 ml MTBE, the solution appeared cloudy. An additional 50 µl of ACN was added to clarify the solution (155 mg/ml ACN: MTBE=1:2). The mixture was left in the vial and capped. Crystals appeared by the next day. The solid was then filtered and placed on a high vacuum line to remove all solvent and give the title compound.

Example 12

Powder X-Ray Diffraction

Powder X-ray diffraction patterns were obtained with a Rigaku diffractometer using Cu Kα (30.0 kV, 15.0 mA) radiation. The analysis was performed with the goniometer running in continuous-scan mode of 3° per minute with a step size of 0.03° over a range of 2 to 450. Samples were prepared on quartz specimen holders as a thin layer of powdered material. The instrument was calibrated with a silicon metal standard.

Figure 8:
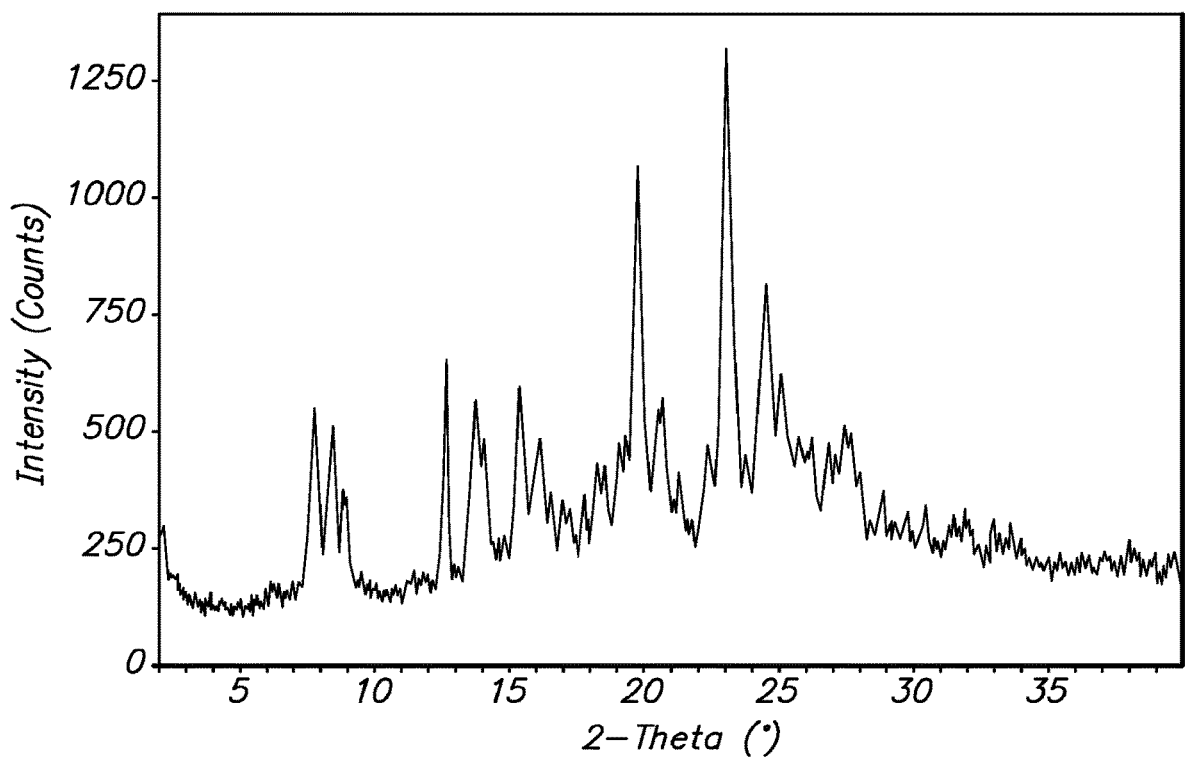
FIG. 8 shows a PXRD pattern of a crystalline monosulfate salt of the compound of formula I. This crystalline salt is further characterized by the TGA trace in FIG. 9, the DSC trace in FIG. 10, the DMS trace in FIG. 11, and the micrographic image in FIG. 12.
Figure 13:
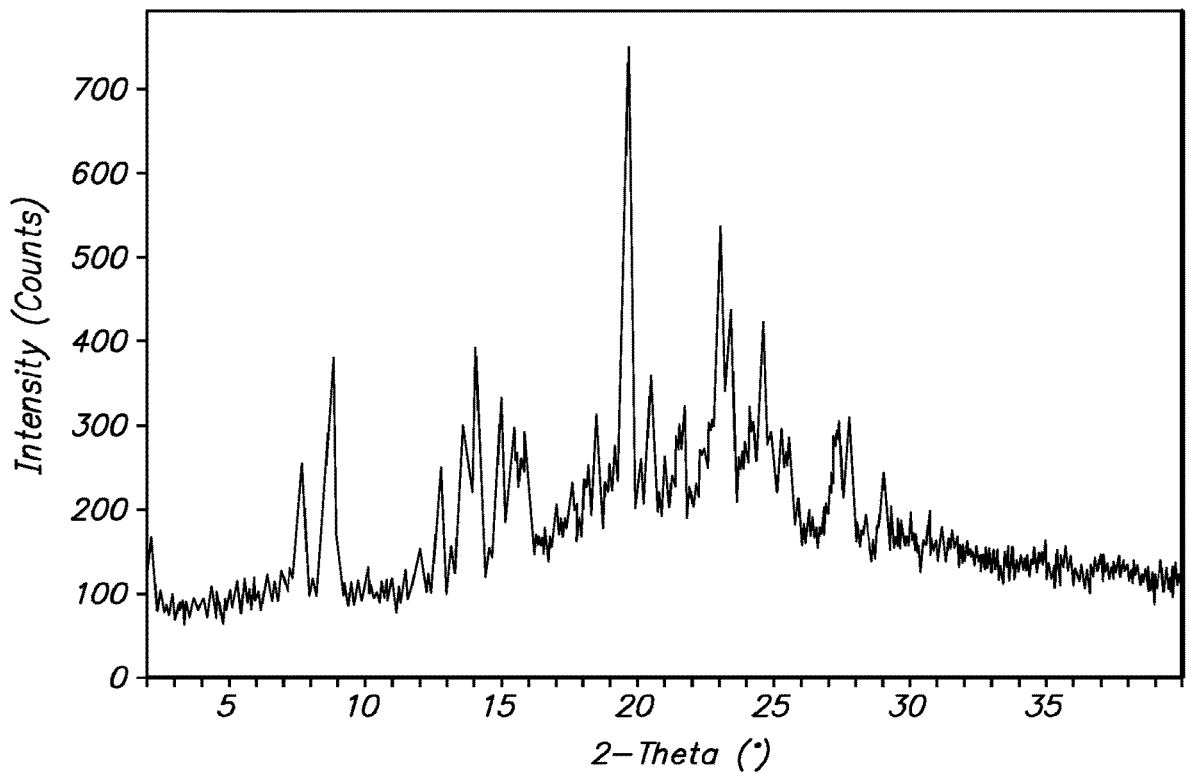
FIG. 13 shows a PXRD pattern of a crystalline dioxalate salt of the compound of formula I. This crystalline salt is further characterized by the TGA trace in FIG. 14, the DSC trace in FIG. 15, the DMS trace in FIG. 16, and the micrographic image in FIG. 17.
Figure 18:
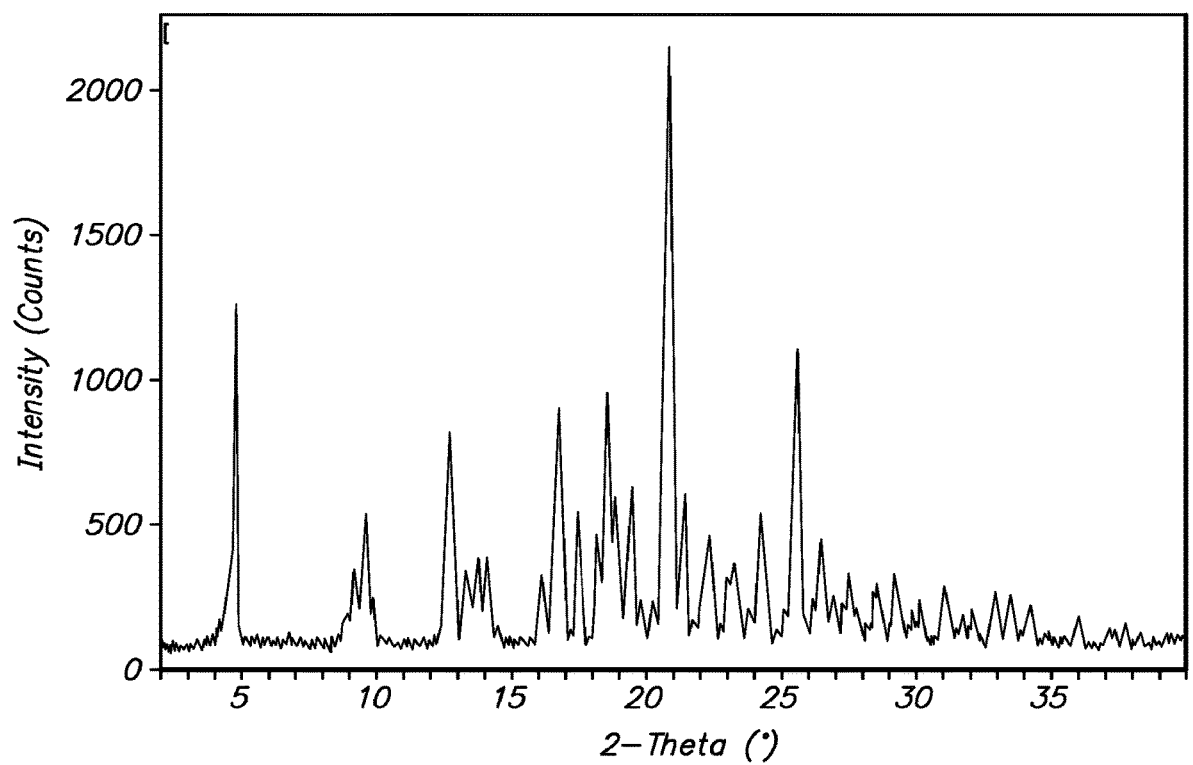
FIG. 18 shows a PXRD pattern of Form I of the crystalline freebase of the compound of formula I. This crystalline freebase is further characterized by the DSC trace in FIG. 19, the TGA trace in FIG. 20, the DMS trace in FIG. 21, and the micrographic image in FIG. 22.
Figure 23:
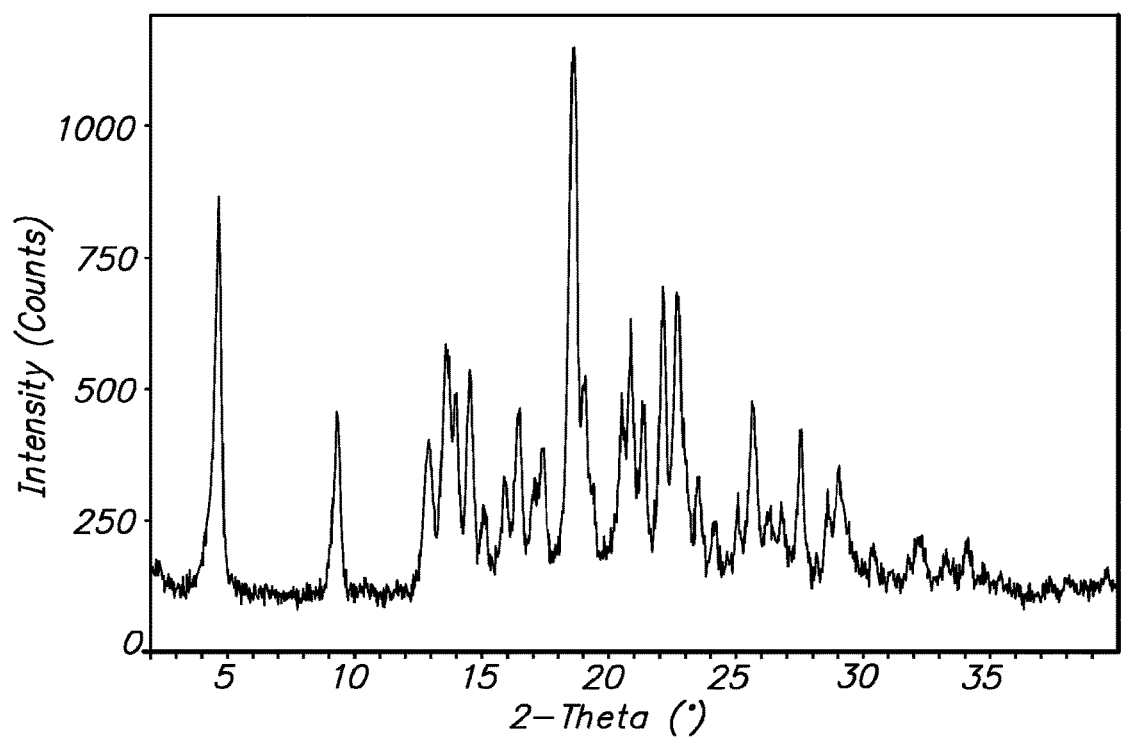
FIG. 23 shows a PXRD pattern of Form II of the crystalline freebase of the compound of formula I. This crystalline freebase is further characterized by the DSC trace in FIG. 24, the TGA trace in FIG. 25, and the DMS trace in FIG. 26.

The PXRD pattern for a sample of the diphosphate salt of Example 2 showed the material to be crystalline. A representative PXRD pattern for a sample of the crystalline diphosphate salt of Example 3 is shown in FIG. 1. The PXRD pattern for a sample of the monosulfate salt of Example 4 showed the material to be crystalline. A representative PXRD pattern for a sample of the crystalline monosulfate salt of Example 5 is shown in FIG. 8. The PXRD pattern for a sample of the dioxalate salt of Example 6 showed the material to be crystalline. A representative PXRD pattern for a sample of the crystalline dioxalate salt of Example 7 is shown in FIG. 13. The PXRD pattern for a sample of the freebase (Form I) of Examples 8 and 9 showed the material to be crystalline. A representative PXRD pattern for a sample of the freebase (Form I) of Example 10 is shown in FIG. 18. A representative PXRD pattern for a sample of the freebase (Form II) of Example 11 is shown in FIG. 23.

Example 13

Thermal Analysis

Differential scanning calorimetry (DSC) was performed using a TA Instruments Model Q-10 module with a Thermal Analyst controller. Data were collected and analyzed using TA Instruments Thermal Solutions software. A sample of about 1-4 mg was accurately weighed into an aluminum pan with lid. The sample was evaluated using a linear heating ramp of 10° C./min from ambient temperature to approximately 300° C. The DSC cell was purged with dry nitrogen during use.

A representative DSC trace for a sample of the crystalline diphosphate salt of Example 3 showed two transitions at about 63.8° C. and 154.3° C., as seen in FIG. 2. This DSC trace demonstrate that this crystalline diphosphate salt has acceptable to good thermal stability with the melting peak at about 154.5° C. and no thermal decomposition below 150° C. The DSC trace also showed an onset of endothermic heat flow at about 135° C.

A representative DSC trace for a sample of the monosulfate salt of Example 4 showed two transitions at about 57° C. and 73.2° C. A representative DSC trace for a sample of the crystalline monosulfate salt of Example 5 showed a transition at 76° C., as seen in FIG. 10, demonstrating that this crystalline monosulfate salt has a melting peak at about 76.5° C.

A representative DSC trace for a sample of the crystalline dioxalate salt of Example 6 showed two transitions at 69.2° C. and 122.8° C. A representative DSC trace for a sample of the crystalline dioxalate salt of Example 7 showed a transition at 73° C., as seen in FIG. 15. This DSC trace demonstrate that this crystalline dioxalate salt has a melting peak at about 73.7° C.

A representative DSC trace for a sample of the crystalline freebase (Form I) of Example 8 showed a transition at 90.4° C. The DSC trace for a sample of the crystalline freebase (Form I) of Example 9 showed two transitions at 86.1° C. and 103.6° C. A representative DSC trace for a sample of the crystalline freebase of Example 10 (Form I) showed two transitions in a closed pan (83.9° C. and 102.1° C.), but one transition at 102.5° C. in an open pan (the early peak is due to water and/or solvents), as seen in FIG. 19. This DSC trace demonstrate that this crystalline freebase has excellent thermal stability with the melting peak at about 102.7° C. and no thermal decomposition below 80° C. The DSC trace also showed an onset of endothermic heat flow at about 90° C.

A representative DSC trace for a sample of the crystalline freebase (Form II) of Example 11 showed a transition at 98.6° C., as seen in FIG. 24, demonstrating that this crystalline freebase has excellent thermal stability with the melting peak at about 98.6° C. and no thermal decomposition below 75° C. The DSC trace also showed an onset of endothermic heat flow at about 75° C.

Thermogravimetric analysis (TGA) was performed using a TA Instruments Model Q-50 module equipped with high resolution capability. Data were collected and analyzed using TA Instruments Thermal Solutions software. A sample weighing about 10 mg was placed onto a platinum pan and scanned with a high resolution-heating rate from ambient temperature to 300° C. The balance and furnace chambers were purged with nitrogen flows during use.

Figure 3:
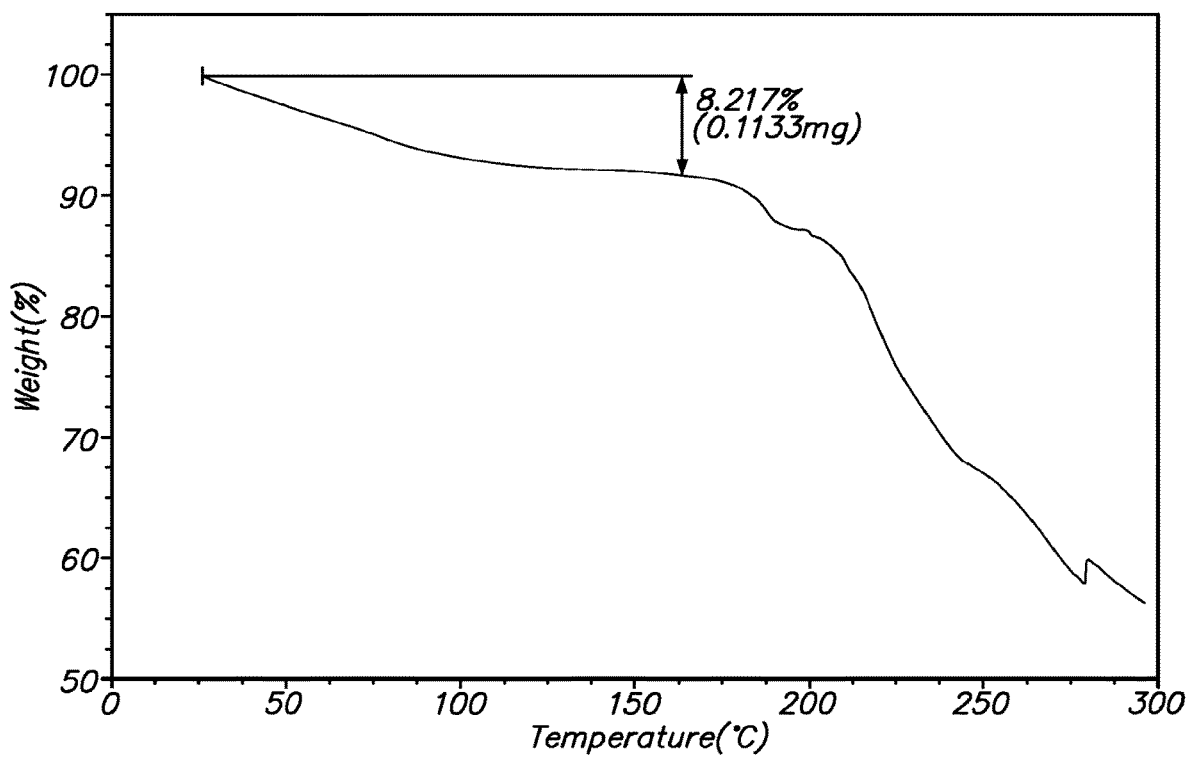
FIG. 3 shows a thermal gravimetric analysis (TGA) trace for this crystalline salt.

A representative TGA trace for a sample of the crystalline diphosphate salt of Example 3 showed a loss of solvents and/or water (8.2%) at temperatures below 155° C., as seen in FIG. 3.

Figure 9:
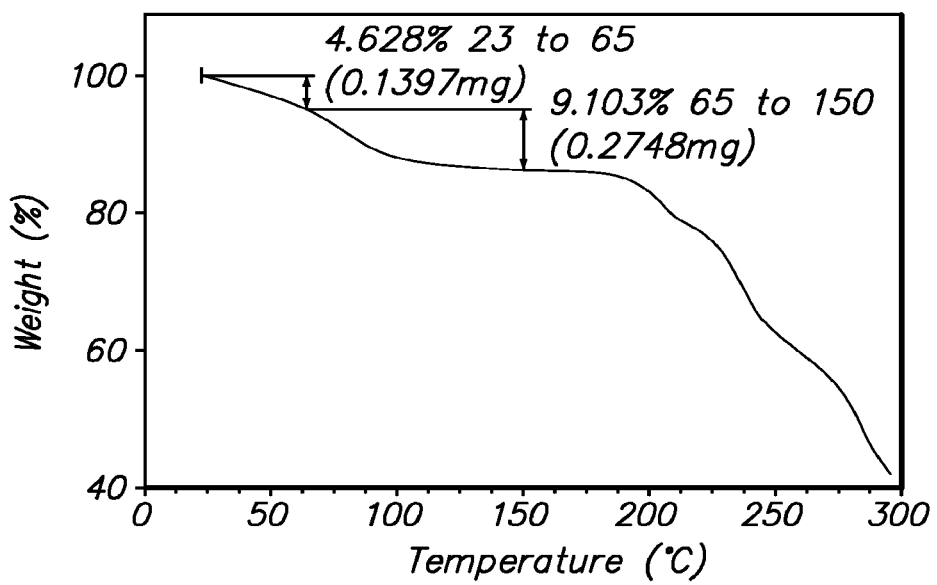

The TGA trace for a sample of the crystalline monosulfate salt of Example 4 showed a loss of solvents and/or water (12.6%) at temperatures below 116° C. A representative TGA trace for a sample of the crystalline monosulfate salt of Example 5 showed a loss of solvents and/or water (13.7%) at temperatures below 150° C., as seen in FIG. 9.

Figure 14:
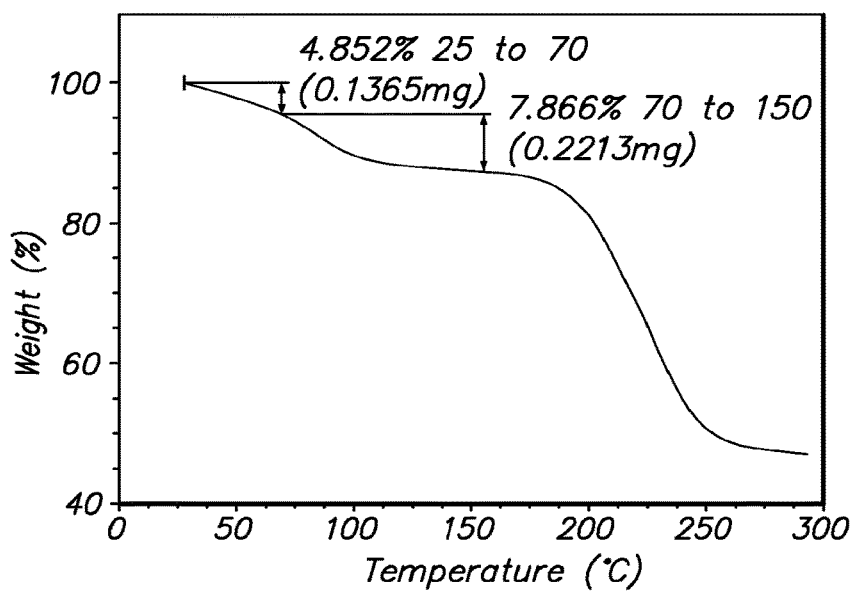

The TGA trace for a sample of the crystalline dioxalate salt of Example 6 showed a loss of solvents and/or water (15.4%) at temperatures below 125° C. A representative TGA trace for a sample of the crystalline dioxalate salt of Example 7 showed a loss of solvents and/or water (12.7%) at temperatures below 125° C., as seen in FIG. 14.

Figure 20:
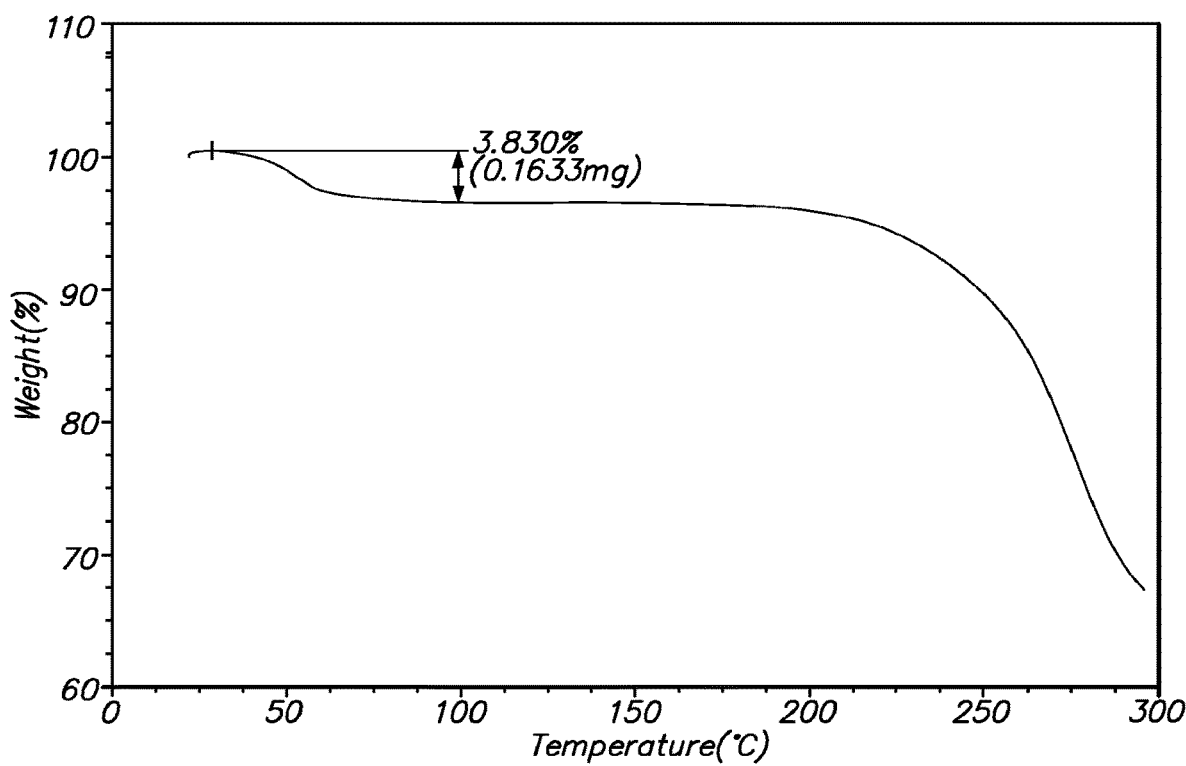

The TGA trace for a sample of the crystalline freebase (Form I) of Example 8 showed a loss of solvents and/or water (7.3%) at temperatures below 75° C. The TGA trace for a sample of the crystalline freebase (Form I) of Example 9 showed a loss of solvents and/or water (5.2%) at temperatures below 70° C. A representative TGA trace for a sample of the crystalline freebase (Form I) of Example 10 showed a loss of solvents and/or water (3.8%) at temperatures below 98° C., as seen in FIG. 20.

Figure 25:
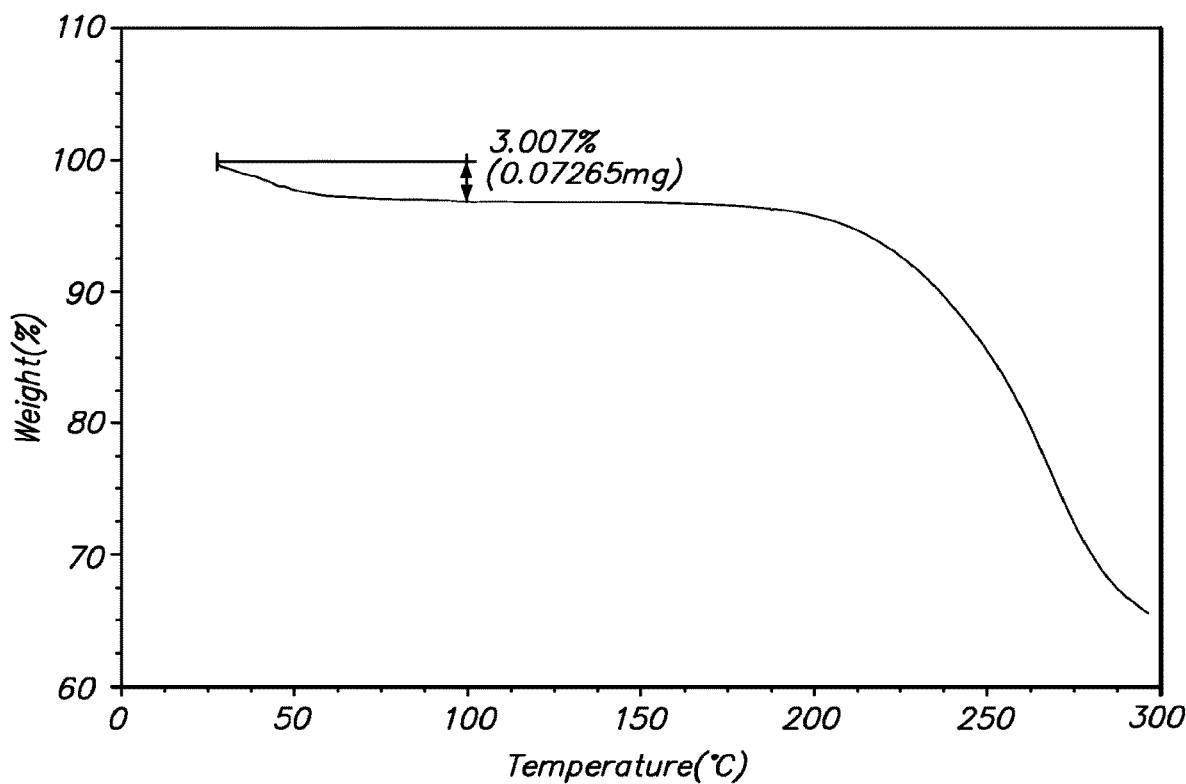

A representative TGA trace for a sample of the crystalline freebase (Form II) of Example 11 showed a loss of solvents and/or water (3.0%) at temperatures below 98° C., as seen in FIG. 25.

These TGA traces indicate that the crystalline compounds of the present invention lose a small amount of weight from room temperature to moderately elevated temperatures (e.g., 75-150° C.), which is consistent with the loss of residual moisture or solvent.

Example 14

Dynamic Moisture Sorption Assessment

A dynamic moisture sorption (DMS) assessment (also known as a moisture sorption-desorption profile) was performed using a VTI atmospheric microbalance, SGA-100 system (VTI Corp., Hialeah, Fla. 33016). A sample size of approximately 10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (+/−5% RH) when the mass of the sample was stable to within 0.01% for 5 consecutive points.

Figure 4:
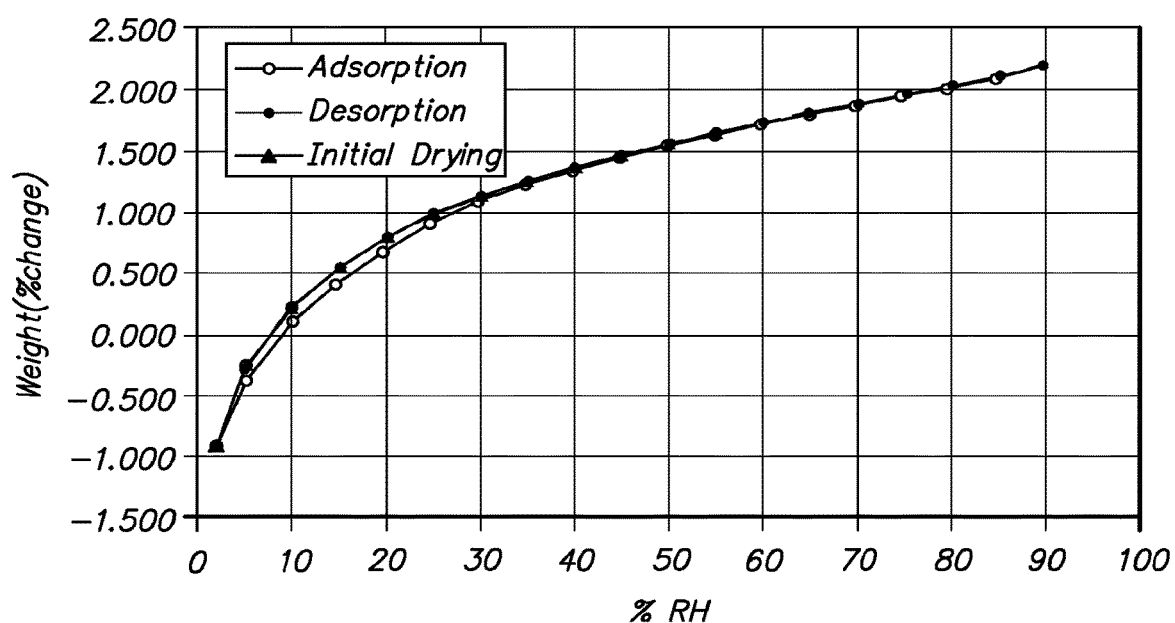
FIG. 4 shows a dynamic moisture sorption (DMS) trace for this crystalline salt.
Figure 5:
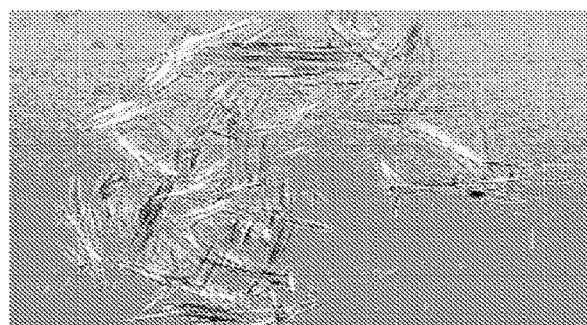
FIG. 5 is a micrographic image of this crystalline salt.

A representative DMS trace for a sample of the crystalline diphosphate salt of Example 3 showed a reversible sorption/desorption profile with low hygroscopicity, with a 3.3% weight gain when exposed to 2-90% RH and a 0.6% weight gain in the humidity range of 40-75% RH, as shown in FIG. 4.

Figure 11:
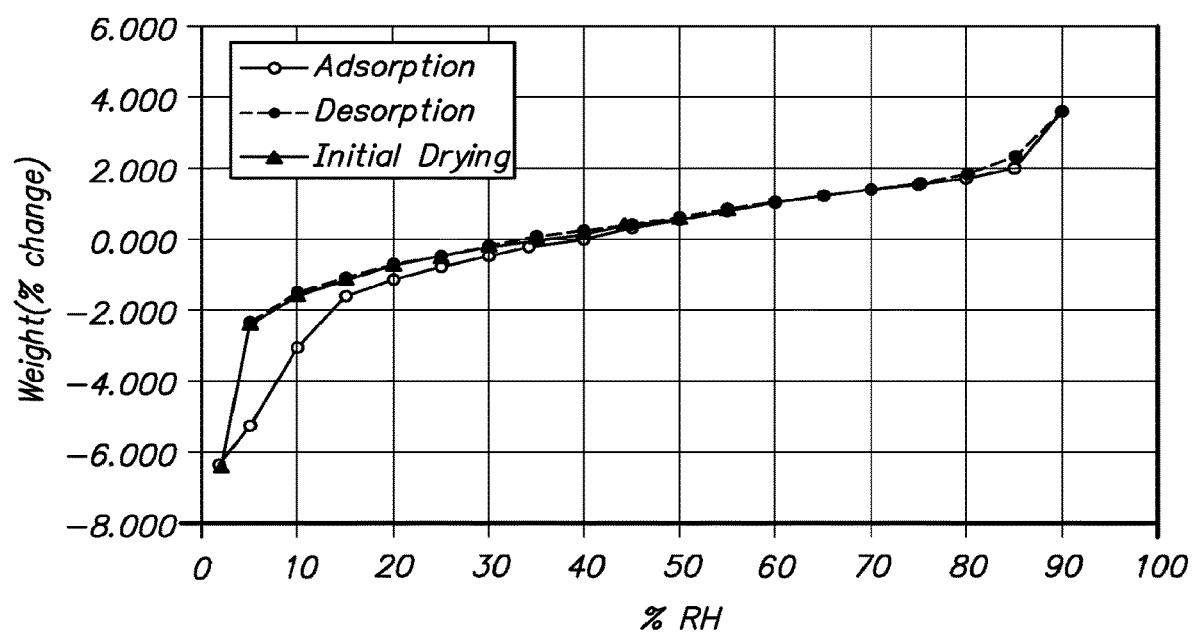
Figure 12:

A representative DMS trace for a sample of the crystalline monosulfate salt of Example 5 showed a reversible sorption/desorption profile with low hygroscopicity, with a 10% weight gain when exposed to 2-90% RH and a 1.8% weight gain in the humidity range of 40-75% RH, as shown in FIG. 11.

Figure 16:
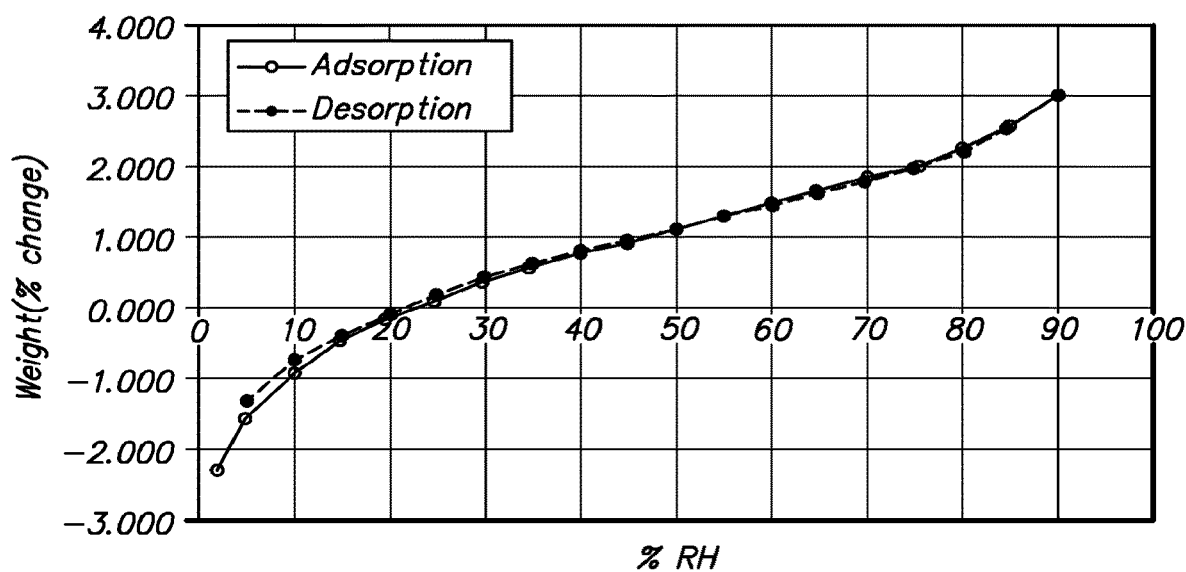
Figure 17:
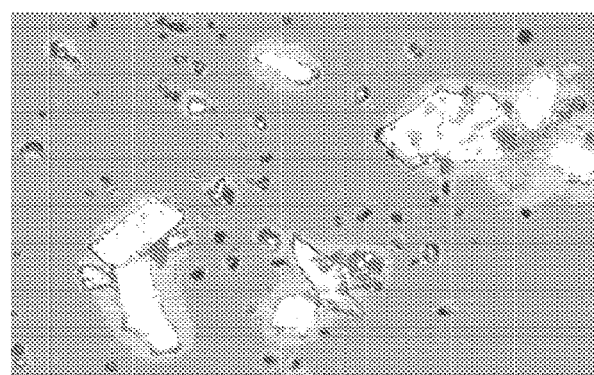

A representative DMS trace for a sample of the crystalline dioxalate salt of Example 7 showed a reversible sorption/desorption profile with low hygroscopicity, with a 5.3% weight gain when exposed to 2-90% RH and a 1.1% weight gain in the humidity range of 40-75% RH, as shown in FIG. 16.

Figure 21:
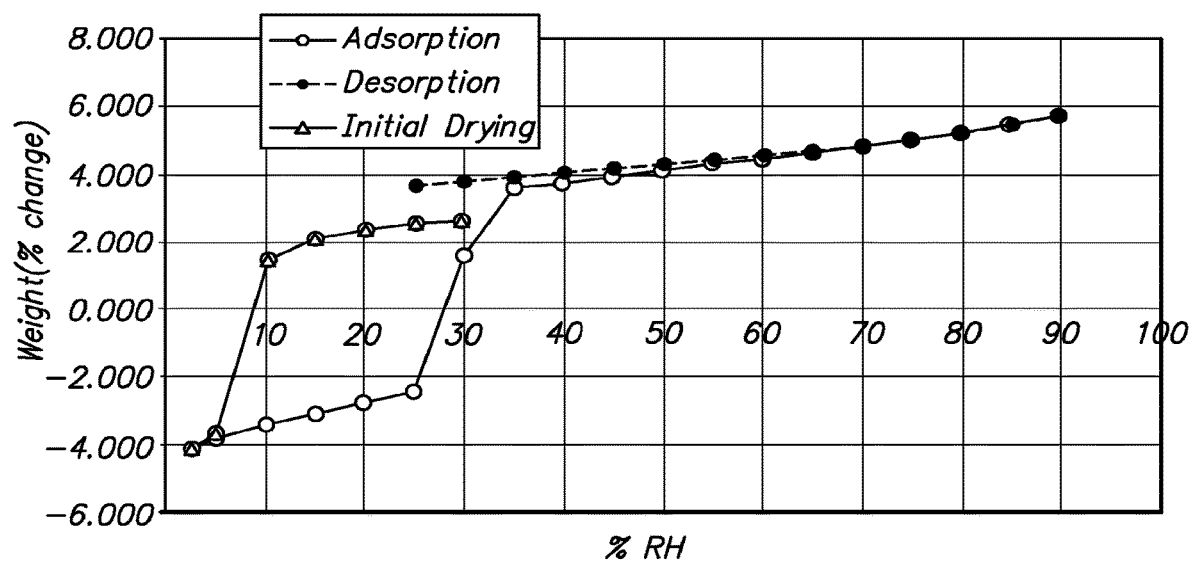
Figure 22:
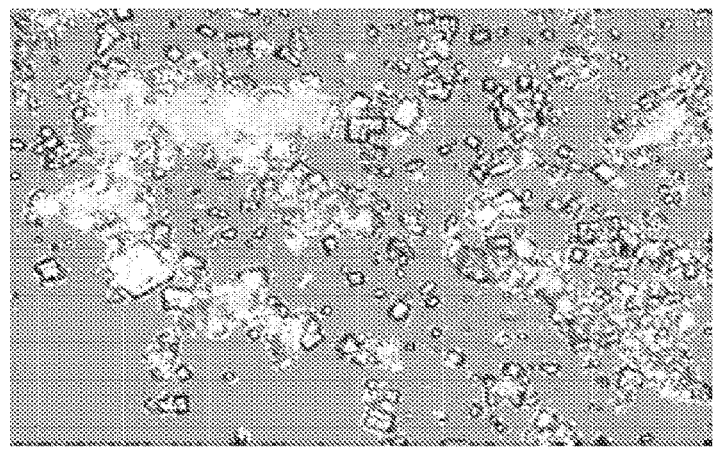

A representative DMS trace for a sample of the crystalline freebase (Form I) of Example 10 showed a reversible sorption/desorption profile with low hygroscopicity, with a 10% weight gain when exposed to 2-90% RH and a 1.2% weight gain in the humidity range of 40-75% RH, as shown in FIG. 21.

Figure 26:
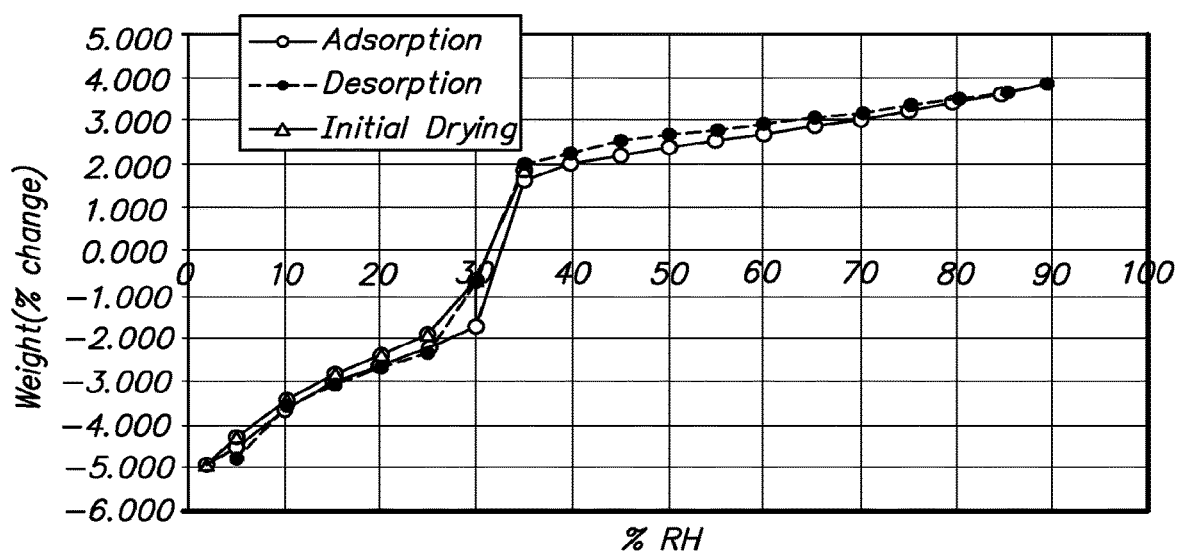

A representative DMS trace for a sample of the crystalline freebase (Form II) of Example 11 showed a reversible sorption/desorption profile with low hygroscopicity, with a 9% weight gain when exposed to 2-90% RH and a 1.3% weight gain in the humidity range of 40-75% RH, as shown in FIG. 26.

These DMS traces demonstrate that the crystalline compounds of the present invention have a reversible sorption/desorption profile with low hygroscopicity. The crystalline compounds have an acceptable weight gain when exposed to a broad humidity range. The reversible moisture sorption/desorption profiles demonstrate that the crystalline compounds of the present invention possess an acceptable hygroscopicity and are not deliquescent.

Example 15

Solid State Stability Assessment

Samples of the crystalline diphosphate salt of Example 3, about 1-2 mg each, were stored in multiple 3 mL borosilicate vials at −20° C. (closed container) and 40° C./75% RH (open and closed container). At specific intervals, the entire contents of a representative vial was analyzed by the following HPLC method:

Column: Xterra Ms C18, 4.6×250 mm, 5 μm (Part No. 186000494); Mobile Phase A: 0.1 M $NH_4Ac$, pH 7.0; Mobile Phase B: 100% ACN; Flow rate: 1 mL/min; Injection Volume: 10 μL; Detector: 240 nm; Gradient—Time in minutes (% Mobile Phase B): 0.0 (8); 5.00 (28); 22.00 (42); 30.00 (100); 35.00 (100); 35.10 (8); and 45.00 (8). Samples were prepared as 0.5 mg/mL stock solutions in 10 mM citrate buffered normal saline, pH 5.

For crystalline diphosphate salt of Example 3, the initial purity of the samples was 98.3% as determined by HPLC area percentage. After storage for six weeks, for the samples kept under all conditions, there was no detectable change in chemical purity, no observable change in the appearance of the material, and analysis by DSC and TGA showed no detectable differences.

Example 16

Elemental Analysis

The following elemental percentages for samples of the crystalline compounds of the invention were determined by combustion analysis using a Flash EA 1112 Elemental Analyzer (CE Elantech, Lakewood, N.J.).

For the crystalline monosulfate salt of Example 5: 52.88% carbon, 7.10% hydrogen, 8.81% nitrogen, 27.17% oxygen, and 4.03% sulfur (expected); 52.11% carbon, 6.90% hydrogen, 8.42% nitrogen, 24.94% oxygen, and 4.06% sulfur (results).

For the crystalline dioxalate salt of Example 7: 54.54% carbon, 6.57% hydrogen, 8.15% nitrogen, and 30.74% oxygen (expected); 56.33% carbon, 6.90% hydrogen, 8.22% nitrogen, and 26.32% oxygen (results).

Example 17

Micronization

A 13 g sample of the crystalline diphosphate salt of Example 3 was micronized with a jet mill to give 8.7 g of a free-flowing white powder with birefringence observed upon microscopic examination (67% recovery). Pre-micronization, the crystalline diphosphate had an initial purity of 98.1% as determined by HPLC area percentage. The purity of the micronized material was the same. The water content of the pre-micronized material was 6.54 wt %, and the water content of the micronized material was 6.23 wt %.

No issues were encountered during the micronization process. Particle size distribution was as follows:

|  | Pre-Micronization | Post-Micronization |
|---|---|---|
| D (v, 0.9) | 38.6 μm | 5.2 μm |
| D (v, 0.5) | 9.9 μm | 2.2 μm |
| D (v, 0.1) | 1.7 μm | 0.4 μm |

No significant changes were observed in the powder x-ray diffraction pattern, TGA, DSC, DMS, chemical purity, chiral purity and moisture content for the micronized material compared to the unmicronized material. For example, as noted in Example 14, a representative DMS trace for a sample of the crystalline diphosphate salt of Example 3 showed a 0.6% weight gain in the humidity range of 40-75% RH, while the micronized material showed a 0.7% weight gain in this humidity range.

Example 18

Inhalation Solution Stability

A solution was prepared with 0.5 mg/mL freebase equivalents (using a crystalline diphosphate salt prepared as described in Example 3) in 10 mM citrate buffered normal saline, pH 5. The solubility of the crystalline salt was greater than 40 mg/mL of freebase equivalent in the buffer. Less than 0.5% degradation was observed after storage for one month at 40° C./75% RH.

Assay 1

Radioligand Binding Assay

Membrane Preparation from Cells Expressing $hM_1$, $hM_2$, $hM_3$ and $hM_4$ Muscarinic Receptor Subtypes CHO cell lines stably expressing cloned human $hM_1$, $hM_2$, $hM_3$ and $hM_4$ muscarinic receptor subtypes, respectively, were grown to near confluency in medium consisting of HAM's F-12 supplemented with 10% FBS and 250 μg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared $hM_5$ receptor membranes were purchased directly from Perkin Elmer and stored at −80° C. until use.

Radioligand Binding Assay on Muscarinic Receptor

Subtypes $hM_1$, $hM_2$, $hM_3$, $hM_4$ and $hM_5$

Radioligand binding assays were performed in 96-well microtiter plates in a total assay volume of 100 μL. CHO cell membranes stably expressing either the $hM_1$, $hM_2$, $hM_3$, hM4 or $hM_5$ muscarinic subtype were diluted in assay buffer to the following specific target protein concentrations (g/well): 10 μg for $hM_1$, 10-15 μg for $hM_2$, 10-20 μg for $hM_3$, 10-20 μg for $hM_4$, and 10-12 μg for $hM_5$. The membranes were briefly homogenized using a Polytron tissue disrupter (10 seconds) prior to assay plate addition. Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were then air dried, and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. *Biochemical Pharmacology* 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. The compound of formula I was found to have a $K_i$ value of less than about 5 nM for the $M_3$ muscarinic receptor subtype when tested in this or a similar assay.

Assay 2

Muscarinic Receptor Functional Potency Assays

Blockade of Agonist-Mediated Inhibition of cAMP Accumulation

In this assay, the functional potency of a test compound was determined by measuring the ability of the test compound to block oxotremorine-inhibition of forskolin-mediated cAMP accumulation in CHO-K1 cells expressing the $hM_2$ receptor.

cAMP assays were performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells were rinsed once with dPBS and lifted with Trypsin-EDTA solution (0.05% trypsin/0.53 mM EDTA) as described in the Cell Culture and Membrane Preparation section above. The detached cells were washed twice by centrifugation at 650×g for five minutes in 50 mLs dPBS. The cell pellet was then re-suspended in 10 mL dPBS, and the cells were counted with a Coulter Z1 Dual Particle Counter (Beckman Coulter, Fullerton, Calif.). The cells were centrifuged again at 650×g for five minutes and re-suspended in stimulation buffer to an assay concentration of $1.6 \times 10^6$-$2.8 \times 10^6$ cells/mL. The test compound was initially dissolved to a concentration of 400 µM in dilution buffer (dPBS supplemented with 1 mg/mL BSA (0.1%)), and then serially diluted with dilution buffer to final molar concentrations ranging from 100:M to 0.1 nM. Oxotremorine was diluted in a similar manner.

To measure oxotremorine inhibition of AC activity, 25 µL forskolin (25 µM final concentration diluted in dPBS), 25 µL diluted oxotremorine, and 50 µL cells were added to agonist assay wells. To measure the ability of a test compound to block oxotremorine-inhibited AC activity, 25 µL forskolin and oxotremorine (25 µM and 5 µM final concentrations, respectively, diluted in dPBS) 25 µL diluted test compound, and 50 µL cells were added to remaining assay wells.

Reactions were incubated for 10 minutes at 37° C. and stopped by addition of 100 µL ice-cold detection buffer. Plates were sealed, incubated overnight at room temperature and counted the next morning on a PerkinElmer TopCount liquid scintillation counter (PerkinElmer Inc., Wellesley, Mass.). The amount of cAMP produced (pmol/well) was calculated based on the counts observed for the samples and cAMP standards, as described in the manufacturer's user manual. Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $EC_{50}$ of the oxotremorine concentration-response curve and the oxotremorine assay concentration as the $K_D$ and [L], respectively. The $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher functional activity at the receptor tested. The compound of formula I was found to have a $K_i$ value of less than about 5 nM for blockade of oxotremorine-inhibition of forskolin-mediated cAMP accumulation in CHO-K1 cells expressing the $hM_2$ receptor, when tested in this or a similar assay.

Blockade of Agonist-Mediated [$^{35}$S]GTPγS-Binding

In a second functional assay, the functional potency of test compounds can be determined by measuring the ability of the compounds to block oxotremorine-stimulated [$^{35}$S] GTPγS-binding in CHO-K1 cells expressing the $hM_2$ receptor.

At the time of use, frozen membranes were thawed and then diluted in assay buffer with a final target tissue concentration of 5-10 µg protein per well. The membranes were briefly homogenized using a Polytron PT-2100 tissue disrupter and then added to the assay plates. The $EC_{90}$ value (effective concentration for 90% maximal response) for stimulation of [$^{35}$S]GTPγS binding by the agonist oxotremorine was determined in each experiment.

To determine the ability of a test compound to inhibit oxotremorine-stimulated [$^{35}$S]GTPγS binding, the following was added to each well of 96 well plates: 25 µL of assay buffer with [$^{35}$S]GTPγS (0.4 nM), 25 µL of oxotremorine ($EC_{90}$) and GDP (3 µM), 25 µL of diluted test compound and 25 µL CHO cell membranes expressing the $hM_2$ receptor. The assay plates were then incubated at 37° C. for 60 minutes. The assay plates were filtered over 1% BSA-pretreated GF/B filters using a PerkinElmer 96-well harvester. The plates were rinsed with ice-cold wash buffer for 3×3 seconds and then air or vacuum dried. Microscint-20 scintillation liquid (50 µL) was added to each well, and each plate was sealed and radioactivity counted on a topcounter (PerkinElmer). Data were analyzed by nonlinear regression analysis with the GraphPad Prism Software package (GraphPad Software, Inc., San Diego, Calif.) using the non-linear regression, one-site competition equation. The Cheng-Prusoff equation was used to calculate the $K_i$, using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. The compound of formula I was found to have a $K_i$ value of less than about 5 nM for blockade of oxotremorine-stimulated [$^{35}$S]GTPγS-binding in CHO-K1 cells expressing the $hM_2$ receptor, when tested in this or a similar assay.

Blockade of Agonist-Mediated Calcium Release Via FLIPR Assays

Muscarinic receptor subtypes ($M_1$, $M_3$ and $M_5$ receptors), which couple to $G_q$ proteins, activate the phospholipase C (PLC) pathway upon agonist binding to the receptor. As a result, activated PLC hydrolyzes phosphatyl inositol diphosphate ($PIP_2$) to diacylglycerol (DAG) and phosphatidyl-1,4,5-triphosphate ($IP_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human $M_1$ and $M_3$, and chimpanzee $M_5$ receptors. Antagonist potency can be determined by the ability of antagonists to inhibit agonist-mediated increases in intracellular calcium.

For FLIPR calcium stimulation assays, CHO cells stably expressing the $hM_1$, $hM_3$ and $cM_5$ receptors are seeded into 96-well FLIPR plates the night before the assay is done.

Seeded cells are washed twice by Cellwash (MTX Labsystems, Inc.) with FLIPR buffer (10 mM HEPES, pH 7.4, 2 mM calcium chloride, 2.5 mM probenecid in HBSS without calcium and magnesium) to remove growth media and leaving 50 µL/well of FLIPR buffer. The cells are then incubated with 50 µL/well of 4 µM FLUO-4AM (a 2× solution was made) for 40 minutes at 37° C., 5% carbon dioxide. Following the dye incubation period, cells are washed two times with FLIPR buffer, leaving a final volume of 50 µL/well.

To determine antagonist potency, the dose-dependent stimulation of intracellular $Ca^{2+}$ release for oxotremorine is first determined so that antagonist potency can later be measured against oxotremorine stimulation at an $EC_{90}$ concentration. Cells are first incubated with compound dilution buffer for 20 minutes, followed by agonist addition, which is performed by the FLIPR. An $EC_{90}$ value for oxotremorine is generated according to the method detailed in the FLIPR measurement and data reduction section below, in conjunction with the formula $EC_F=((F/100-F)^\wedge/H)*EC_{50}$. An oxotremorine concentration of $3 \times EC_F$ is prepared in stimulation plates such that an $EC_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change.

The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response. Antagonist $K_i$ values are determined by Prism using the oxotremorine $EC_{50}$ value as the $K_D$ and the oxotremorine $EC_{90}$ for the ligand concentration according to the Cheng-Prusoff equation (Cheng & Prusoff, 1973).

In this assay, a lower $K_i$ value indicates that the test compound has a higher functional activity at the receptor tested. The compound of formula I was found to have a $K_i$ value of less than about 5 nM for blockade of agonist-mediated calcium release in CHO cells stably expressing the $hM_3$ receptor, when tested in this or a similar assay.

Assay 3

Determination of Duration of Bronchoprotection in Guinea Pig Model of Acetylcholine-Induced Bronchoconstriction This in vivo assay is used to assess the bronchoprotective effects of test compounds exhibiting muscarinic receptor antagonist activity. Groups of six male guinea pigs (Duncan-Hartley (HsdPoc:DH) Harlan, Madison, Wis.) weighing between 250 and 350 g are individually identified by cage cards. Throughout the study animals are allowed access to food and water ad libitum.

Test compounds are administered via inhalation over 10 minutes in a whole-body exposure dosing chamber (R&S Molds, San Carlos, Calif.). The dosing chambers are arranged so that an aerosol was simultaneously delivered to 6 individual chambers from a central manifold. Guinea pigs are exposed to an aerosol of a test compound or vehicle (WFI). These aerosols are generated from aqueous solutions using an LC Star Nebulizer Set (Model 22F51, PARI Respiratory Equipment, Inc. Midlothian, Va.) driven by a mixture of gases ($CO_2=5\%$, $O_2=21\%$ and $N_2=74\%$) at a pressure of 22 psi. The gas flow through the nebulizer at this operating pressure is approximately 3 L/minute. The generated aerosols are driven into the chambers by positive pressure. No dilution air is used during the delivery of aerosolized solutions. During the 10 minute nebulization, approximately 1.8 mL of solution is nebulized. This is measured gravimetrically by comparing pre- and post-nebulization weights of the filled nebulizer.

The bronchoprotective effects of test compounds administered via inhalation are evaluated using whole body plethysmography at 1.5, 24, 48 and 72 hours post-dose.

Forty-five minutes prior to the start of the pulmonary evaluation, each guinea pig is anesthetized with an intramuscular injection of ketamine (43.75 mg/kg), xylazine (3.50 mg/kg) and acepromazine (1.05 mg/kg). After the surgical site is shaved and cleaned with 70% alcohol, a 2-3 cm midline incision of the ventral aspect of the neck was made. Then, the jugular vein is isolated and cannulated with a saline-filled polyethylene catheter (PE-50, Becton Dickinson, Sparks, Md.) to allow for intravenous infusions of ACh (Sigma-Aldrich, St. Louis, Mo.) in saline. The trachea is then dissected free and cannulated with a 14G teflon tube (# NE-014, Small Parts, Miami Lakes, Fla.). If required, anesthesia is maintained by additional intramuscular injections of the aforementioned anesthetic mixture. The depth of anesthesia is monitored and adjusted if the animal responds to pinching of its paw or if the respiration rate is greater than 100 breaths/minute.

Once the cannulations are complete, the animal is placed into a plethysmograph (# PLY3114, Buxco Electronics, Inc., Sharon, Conn.) and an esophageal pressure cannula (PE-160, Becton Dickinson, Sparks, Md.) is inserted to measure pulmonary driving pressure (pressure). The teflon tracheal tube is attached to the opening of the plethysmograph to allow the guinea pig to breathe room air from outside the chamber. The chamber is then sealed. A heating lamp is used to maintain body temperature and the guinea pig's lungs are inflated 3 times with 4 mL of air using a 10 mL calibration syringe (#5520 Series, Hans Rudolph, Kansas City, Mo.) to ensure that the lower airways do not collapse and that the animal does not suffer from hyperventilation.

Once it is determined that baseline values are within the range 0.3-0.9 mL/cm $H_2O$ for compliance and within the range 0.1-0.199 cm $H_2O$/mL per second for resistance, the pulmonary evaluation is initiated. A Buxco pulmonary measurement computer progam enables the collection and derivation of pulmonary values.

Starting this program initiates the experimental protocol and data collection. The changes in volume over time that occur within the plethysmograph with each breath are measured via a Buxco pressure transducer. By integrating this signal over time, a measurement of flow is calculated for each breath. This signal, together with the pulmonary driving pressure changes, which are collected using a Sensym pressure transducer (# TRD4100), is connected via a Buxco (MAX 2270) preamplifier to a data collection interface (#'s SFT3400 and SFT3813). All other pulmonary parameters are derived from these two inputs.

Baseline values are collected for 5 minutes, after which time the guinea pigs are challenged with ACh. ACh (0.1 mg/mL) is infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance has not returned to baseline values at 3 minutes following each ACh dose, the guinea pig's lungs are inflated 3 times with 4 mL of air from a 10 mL calibration syringe. Recorded pulmonary parameters includes respiration frequency (breaths/minute), compliance (mL/cm $H_2O$) and pulmonary resistance (cm $H_2O$/mL per second). Once the pulmonary function measurements are completed at minute 35 of this protocol, the guinea pig is removed from the plethysmograph and euthanized by carbon dioxide asphyxiation.

The data are evaluated in one or both of the following ways:

(a) Pulmonary resistance ($R_L$, cm $H_2O$/mL per second) is calculated from the ratio of "change in pressure" to "the change in flow." The $R_L$ response to ACh (60 µg/min, IH) is computed for the vehicle and the test compound groups. The mean ACh response in vehicle-treated animals, at each pre-treatment time, is calculated and used to compute % inhibition of ACh response, at the corresponding pre-treatment time, at each test compound dose. Inhibition dose-response curves for '$R_L$' are fitted with a four parameter logistic equation using GraphPad Prism, version 3.00 for Windows (GraphPad Software, San Diego, Calif.) to estimate bronchoprotective $ID_{50}$ (dose required to inhibit the ACh (60 µg/min) bronchoconstrictor response by 50%). The equation used is as follows:

$$Y = Min + (Max - Min)/(1 + 10^{((log\ ID50 - X)*Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of ACh or histamine needed to cause a doubling of the baseline pulmonary resistance, is calculated using the pulmonary resistance values derived from the flow and the pressure over a range of ACh or histamine challenges using the following equation (which is derived from a equation used to calculate $PC_{20}$ values described in American Thoracic Society. Guidelines for methacholine and exercise challenge testing—1999. *Am J Respir Crit Care Med.* 161: 309-329 (2000)):

$$PD_2 = antilog\left[log\ C_1 + \frac{(log\ C_2 - log\ C_1)(2R_0 - R_1)}{R_2 - R_1}\right]$$

where: $C_1$ is the concentration of ACh or histamine preceding $C_2$; $C_2$ is the concentration of ACh or histamine resulting in at least a 2-fold increase in pulmonary resistance ($R_L$); $R_0$ is the baseline $R_L$ value; $R_1$ is the $R_L$ value after $C_1$; and $R_2$ is the $R_L$ value after $C_2$. An efficacious dose is defined as a dose that limits the bronchrestriction response to a 50 µg/mL dose of ACh to a doubling of the baseline pulmonary resistance ($PD_{2(50)}$).

Statistical analysis of the data is performed using a two-tailed Students t-test. A P-value<0.05 is considered significant. Generally, test compounds having a $PD_{2(50)}$ less than about 200 µg/mL for ACh-induced bronchoconstriction at 1.5 hours post-dose in this assay are preferred. The compound of formula I is expected to have a $PD_{2(50)}$ less than about 200 µg/mL for ACh-induced bronchoconstriction at 1.5 hours post-dose, when tested in this or a similar assay.

Assay 4

Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (IH) over a 10 minute time period in a pie shaped dosing chamber (R&S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment.

Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, SC) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol* 24:243-254 (1996).

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The following equation is used:

$$Y = Min + (Max - Min)/(1 + 10^{((log\ ID50 - X)*Hillslope)})$$

where X is the logarithm of dose, Y is the response (% inhibition of salivation). Y starts at Min and approaches asymptotically to Max with a sigmoidal shape.

The ratio of the anti-sialagogue $ID_{50}$ to bronchoprotective $ID_{50}$ is used to compute the apparent lung selectivity index of the test compound. Generally, compounds having an apparent lung selectivity index greater than about 5 are preferred. The compound of formula I is expected to have an apparent lung-selectivity index greater than about 5, when tested in this or a similar assay.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g are used in these studies. Under isoflurane anesthesia (to effect), animals are instrumented with common carotid artery and jugular vein catheters (PE-50 tubing). The catheters are exteriorized utilizing a subcutaneous tunnel to the subscapular area. All surgical incisions are sutured with 4-0 Ethicon Silk and the catheters locked with heparin (1000 units/mL). Each animal is administered saline (3 mL, SC) at the end of surgery as well as buprenorphine (0.05 mg/kg, IM). Animals are allowed to recover on a heating pad before being returned to their holding rooms.

Approximately 18 to 20 hours following surgery, the animals are weighed and the carotid artery catheter on each animal is connected to a transducer for recording arterial pressure. Arterial pressure and heart rate are recorded using a Biopac MP-100 Acquisition System. Animals are allowed to acclimate and stabilize for a period of 20 minutes.

Each animal is challenged with MCh (0.3 mg/kg, IV) administered through the jugular venous line and the cardiovascular response is monitored for 10 minutes. The animals are then placed into the whole body dosing chamber, which is connected to a nebulizer containing the test compound or vehicle solution. The solution is nebulized for 10 minutes using a gas mixture of breathable air and 5% carbon dioxide with a flow rate of 3 liters/minute. The animals are then removed from the whole body chamber and returned to their respective cages. At 1.5 and 24 hours post-dosing, the animals are re-challenged with MCh (0.3 mg/kg, IV) and the hemodynamic response is determined. Thereafter, the animals are euthanized with sodium pentobarbital (150 mg/kg, IV).

MCh produces a decrease in mean arterial pressure (MAP) and decrease in heart rate (bradycardia). The peak decrease, from baseline, in MAP (depressor responses) is measured for each MCh challenge (before and after IH dosing). The effects of treatment on the MCh responses are expressed as % inhibition (mean+/−SEM) of the control depressor responses. Two-way ANOVA with the appropriate post-hoc test is used to test the effects of treatment and pre-treatment time. The depressor responses to MCh are expected to be relatively unchanged at 1.5 and 24 hours after inhalation dosing with vehicle.

The ratio of the anti-depressor $ID_{50}$ to bronchoprotective $ID_{50}$ is used to compute apparent lung-selectivity of the test compound. Generally, compounds having an apparent lung-selectivity index greater than 5 are preferred. The compound of formula I is expected to have an apparent lung-selectivity index greater than 5, when tested in this or a similar assay.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A method for treating chronic obstructive pulmonary disease or asthma in a patient, the method comprising administering to the patient a crystalline salt of biphenyl-2-ylcarbamic acid 1-(2-{[4-(4-carbamoylpiperidin-1-ylmethyl)benzoyl]-methylamino}ethyl)piperidin-4-yl ester and phosphoric acid in a molar ratio of from about 1:1.8 to about 1:2.2; wherein the crystalline salt is characterized by:
   (a) a powder x-ray diffraction pattern having two or more diffraction peaks at 2θ values selected from 6.4±0.2, 7.6±0.2, 8.6±0.2, 13.7±0.2, 15.0±0.2, 19.4±0.2, 21.6±0.2, 22.1±0.2, 22.9±0.2, and 23.7±0.2; or
   (b) a differential scanning calorimetry trace which shows a maximum endothermic heat flow at about 154.5° C.

2. The method of claim 1, wherein the molar ratio is from about 1:1.9 to about 1:2.1.

3. The method of claim 1, wherein the patient is treated for chronic obstructive pulmonary disease.

4. The method of claim 1, wherein the patient is treated for asthma.

5. The method of claim 1, wherein the crystalline salt is characterized by a powder x-ray diffraction pattern having two or more diffraction peaks at 2θ values selected from 6.4±0.2, 7.6±0.2, 8.6±0.2, 13.7±0.2, 15.0±0.2, 19.4±0.2, 21.6±0.2, 22.1±0.2, 22.9±0.2, and 23.7±0.2.

6. The method of claim 5, wherein the powder x-ray diffraction pattern comprises diffraction peaks at 2θ values of 15.0±0.2, 19.4±0.2, 21.6±0.2, and 23.7±0.2.

7. The method of claim 1, wherein the crystalline salt is characterized by a differential scanning calorimetry trace which shows a maximum endothermic heat flow at about 154.5° C.

* * * * *